United States Patent
Mershin et al.

(10) Patent No.: US 9,834,747 B2
(45) Date of Patent: Dec. 5, 2017

(54) METHODS AND APPARATUS FOR TRANSPLANTATION OF NUCLEIC ACID MOLECULES

(71) Applicants: Andreas Mershin, Cambridge, MA (US); James Pelletier, Cambridge, MA (US); Neil Gershenfeld, Cambridge, MA (US); John Glass, Germantown, MD (US); Elizabeth Strychalski, North Potomac, MD (US)

(72) Inventors: Andreas Mershin, Cambridge, MA (US); James Pelletier, Cambridge, MA (US); Neil Gershenfeld, Cambridge, MA (US); John Glass, Germantown, MD (US); Elizabeth Strychalski, North Potomac, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 599 days.

(21) Appl. No.: 14/449,106

(22) Filed: Jul. 31, 2014

(65) Prior Publication Data
US 2015/0037890 A1 Feb. 5, 2015

Related U.S. Application Data

(60) Provisional application No. 61/860,626, filed on Jul. 31, 2013.

(51) Int. Cl.
*C12N 15/04* (2006.01)
*C12M 1/42* (2006.01)
*C12N 15/87* (2006.01)

(52) U.S. Cl.
CPC .............. *C12M 35/08* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 5,273,902 A * | 12/1993 | Frischer | C12N 15/74 435/252.1 |
| 6,086,913 A | 7/2000 | Tam et al. | |
| 8,616,227 B1 | 12/2013 | Facer et al. | |
| 2003/0235839 A1 | 12/2003 | McKernan et al. | |
| 2004/0121449 A1 | 6/2004 | Pugia et al. | |
| 2005/0053952 A1 | 3/2005 | Hong et al. | |

(Continued)

FOREIGN PATENT DOCUMENTS

WO 2012170560 A2 12/2012

OTHER PUBLICATIONS

Huang et al "An electroporation microchip system for the transfection of zebrafissh embryos using quantum dots and GFP genes for evlauation" Biomed. Microdevices, 2007, 9: 761-768.*

(Continued)

*Primary Examiner* — Betty J Forman
(74) *Attorney, Agent, or Firm* — Stephen R. Otis

(57) ABSTRACT

In exemplary implementations, transplantation of nucleic acids into cells occurs in microfluidic chambers. The nucleic acids may be large nucleic acid molecules with more than 100 kbp. In some cases, the microfluidic chambers have only one orifice that opens to a flow channel. In some cases, flow through a microfluidic chamber temporarily ceases due to closing one or more valves. Transplantation occurs during a period in which the contents of the chambers are shielded from shear forces. Diffusion, centrifugation, suction from a vacuum channel, or dead-end loading may be used to move cells or buffers into the chambers.

8 Claims, 16 Drawing Sheets

(56) References Cited

U.S. PATENT DOCUMENTS

| | | | |
|---|---|---|---|
| 2005/0129581 A1 | 6/2005 | McBride et al. | |
| 2008/0081372 A1* | 4/2008 | Huang | C12M 35/02 435/440 |
| 2010/0152054 A1* | 6/2010 | Love | B82Y 30/00 506/9 |
| 2011/0053272 A1 | 3/2011 | Benders et al. | |
| 2011/0159511 A1 | 6/2011 | Lenhard et al. | |
| 2011/0207222 A1 | 8/2011 | Mehta et al. | |
| 2011/0213288 A1* | 9/2011 | Choi | C12M 23/16 604/6.08 |
| 2012/0006760 A1 | 1/2012 | Toner et al. | |
| 2012/0258487 A1 | 10/2012 | Chang et al. | |
| 2013/0005025 A1 | 1/2013 | Church et al. | |
| 2013/0115606 A1 | 5/2013 | Hansen et al. | |

OTHER PUBLICATIONS

Balaban, N., et al., 2004, Bacterial Persistence as a Phenotypic Switch. Science Sep. 10, 2004, vol. 305 No. 5690 pp. 1622-1625.

Karas, B., et al., 2013, Direct transfer of whole genomes from bacteria to yeast. Nature Methods 10,410-412 (2013).

Lartigue, C., et al., 2007, Genome Transplantation in Bacteria: Changing One Species to Another. Science Aug. 3, 2007, vol. 317 No. 5838 pp. 632-638.

Le Pioufle, B., et al., 2000, Living cells captured on a bio-microsystem devoted to DNA injection. Materials Science and Engineering: C, vol. 12, Issues 1-2, Aug. 18, 2000, pp. 77-81.

Lin, J., et al., 2011, Development of an integrated microfluidic perfusion cell culture system for real-time microscopic observation of biological cells. Sensors (Basel). 2011;11(9): 8395-411.

Nagamine, K., et al., 2005, On-chip transformation of bacteria. Anal Chem. Jul. 1, 2005;77(13): 4278-81.

Pelletier, J., et al., 2012, Physical manipulation of the *Escherichia coli* chromosome reveals its soft nature. Proceedings of the National Academy of Sciences of the United States of America, vol. 109, No. 40, 15978-15979, Oct. 2, 2012.

Wang, P., et al., 2010, Robust growth of *Escherichia coli*. Current Biology, Jun. 22, 2010;20(12):1099-103.

\* cited by examiner

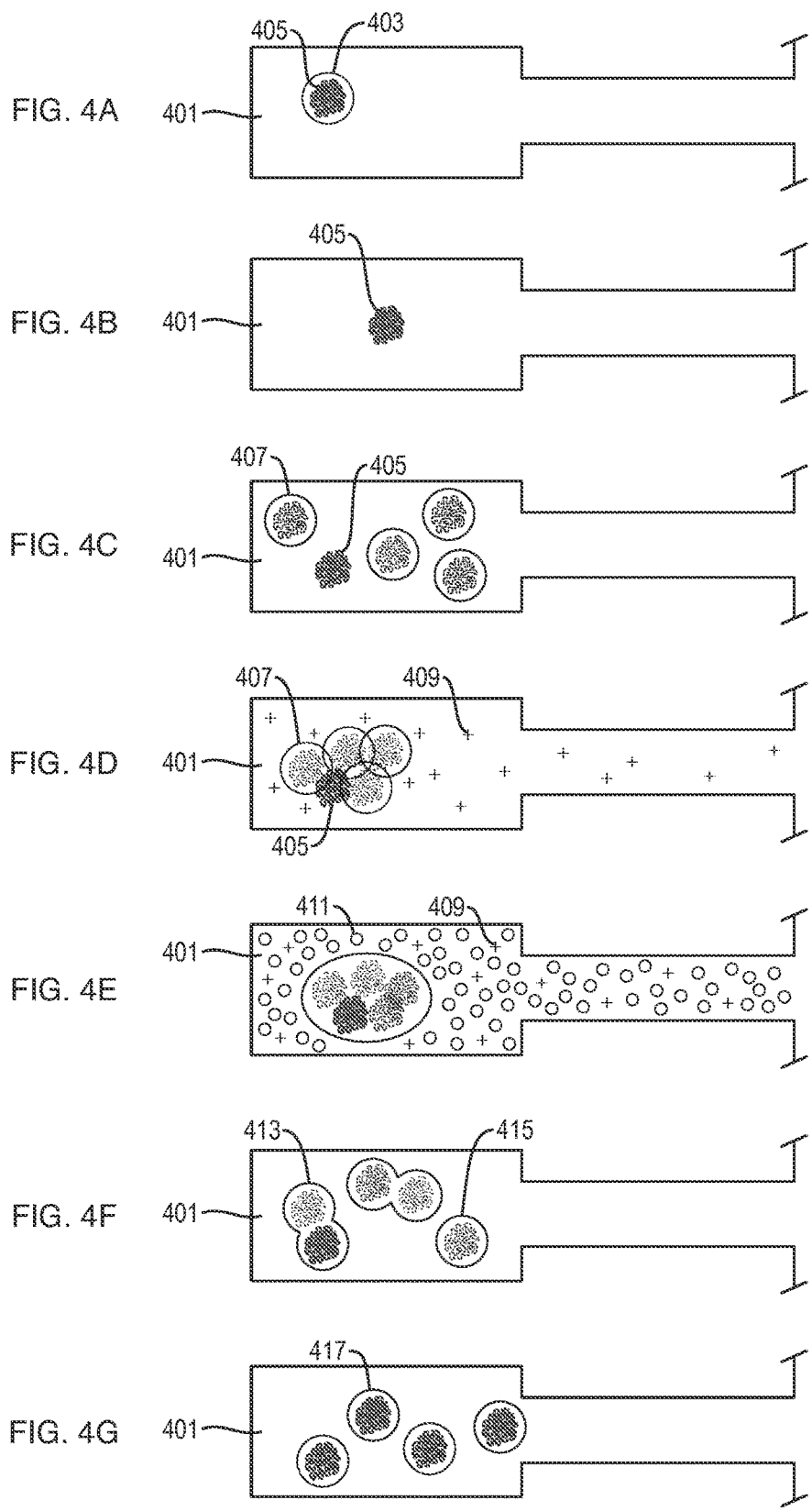

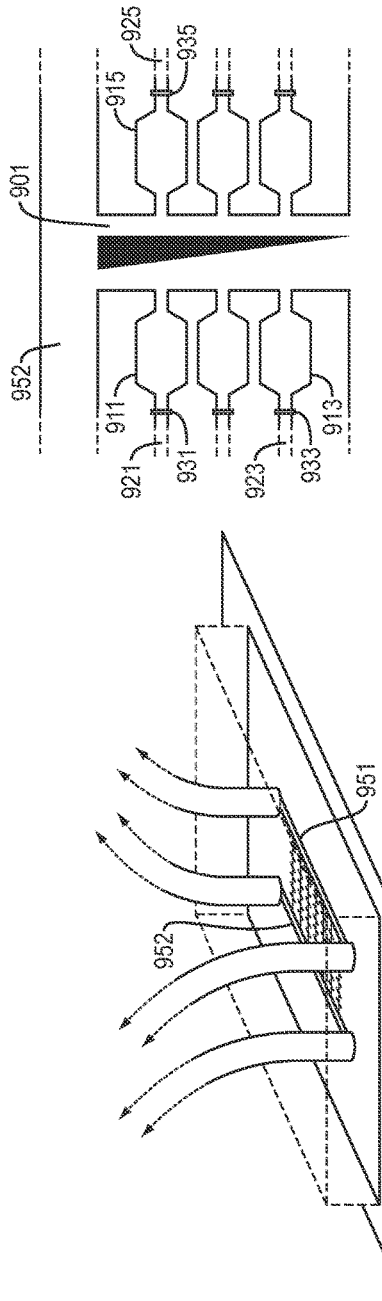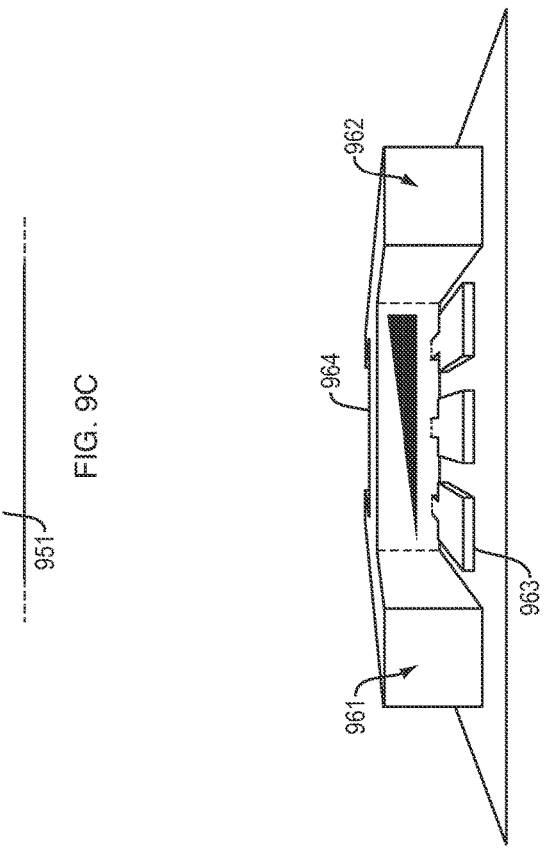

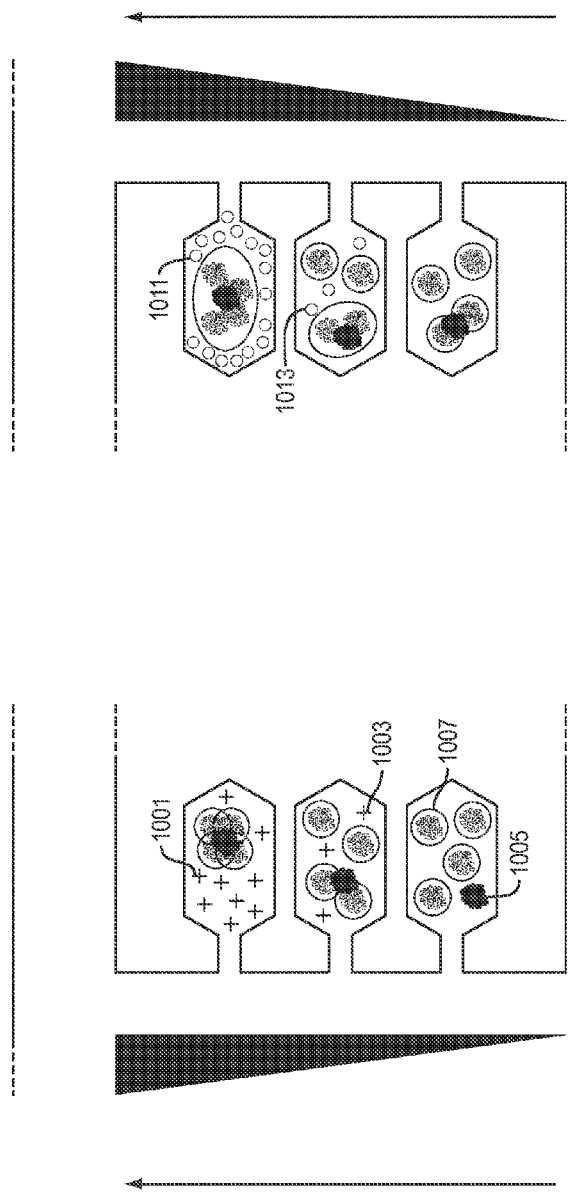
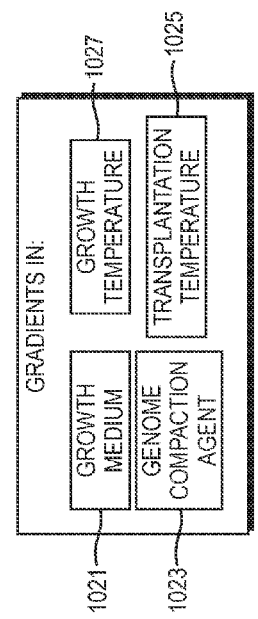
FIG. 10A
FIG. 10B
FIG. 10C

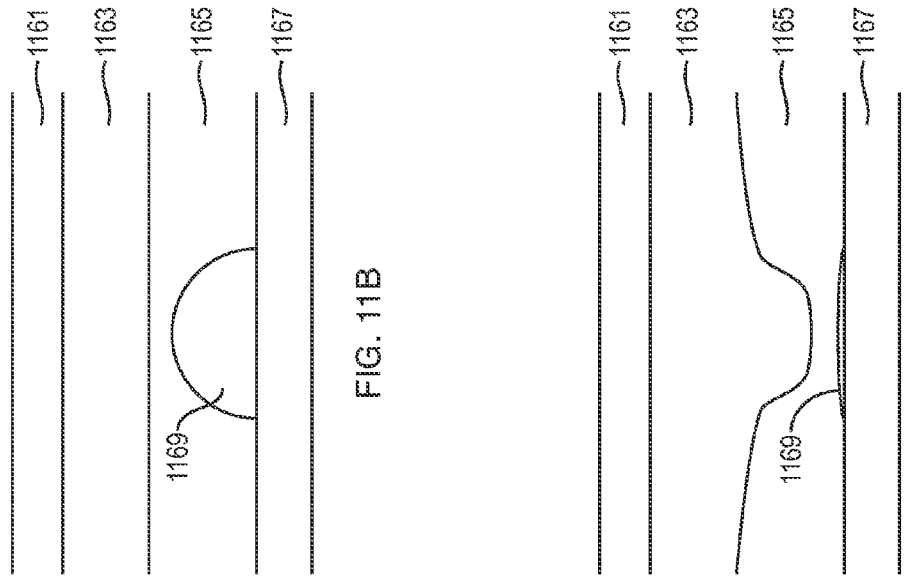
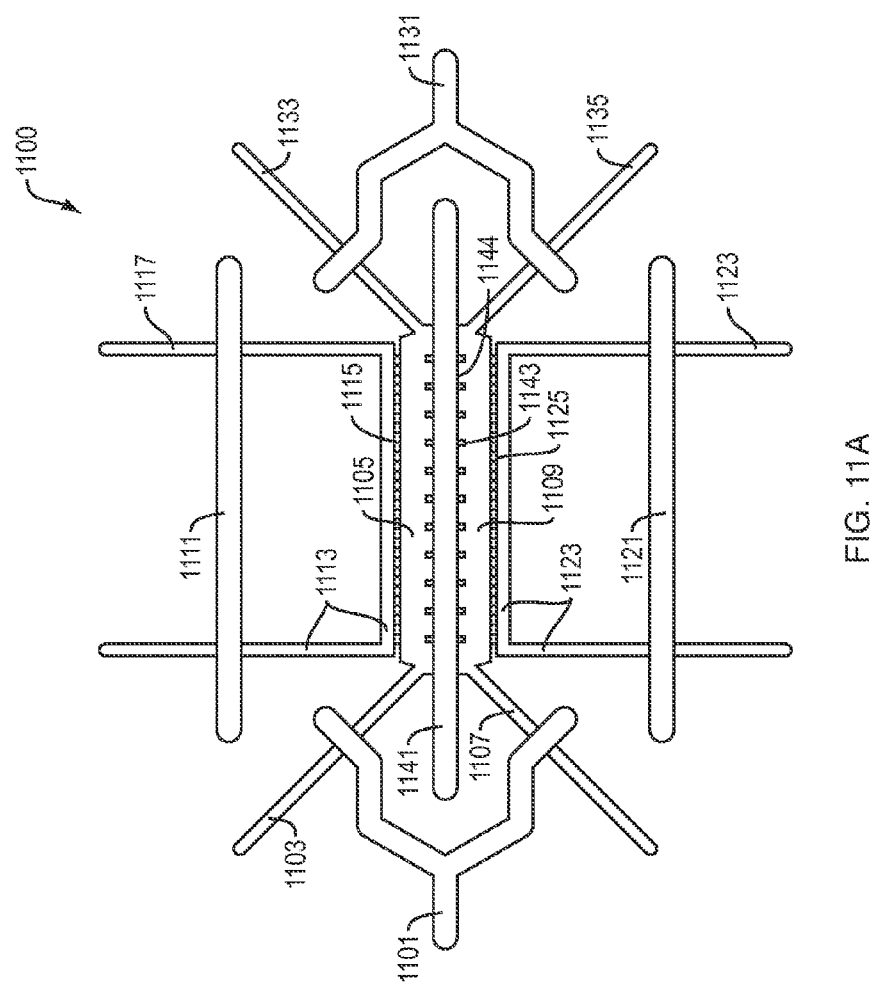

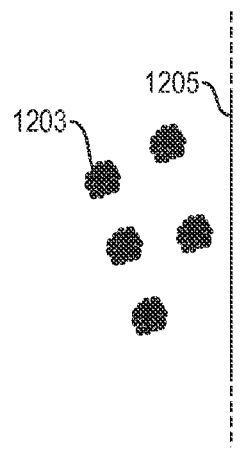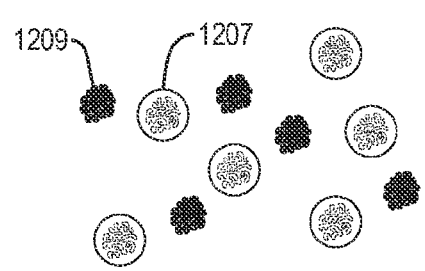
FIG. 12A    FIG. 12B
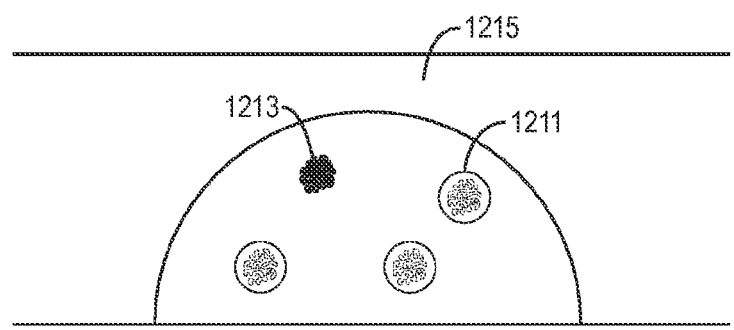
FIG. 12C
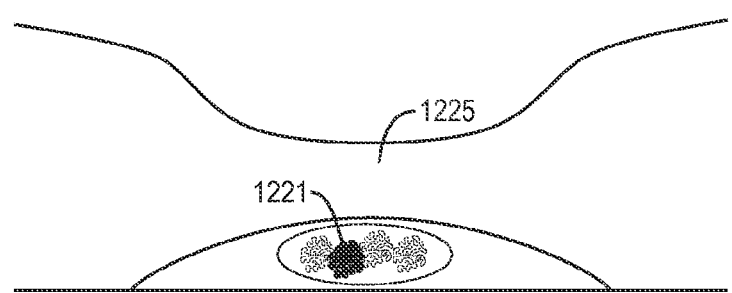
FIG. 12D

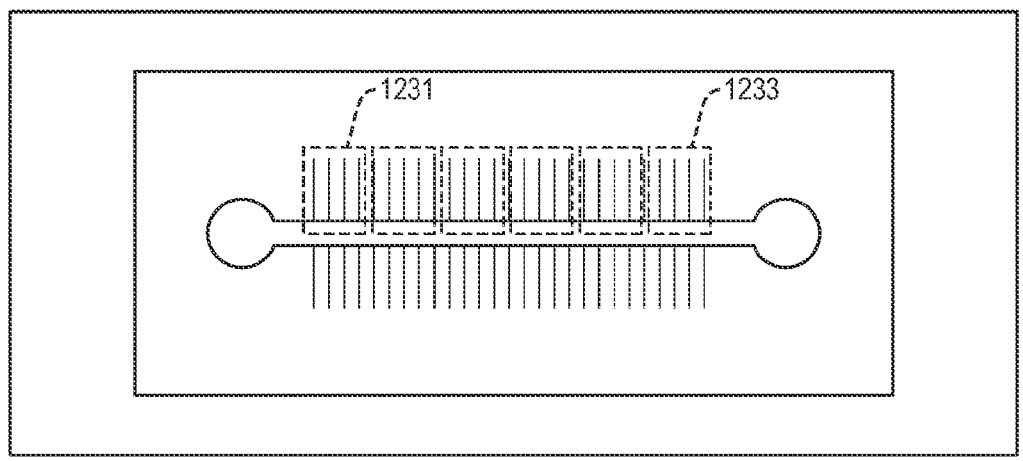
FIG. 12E
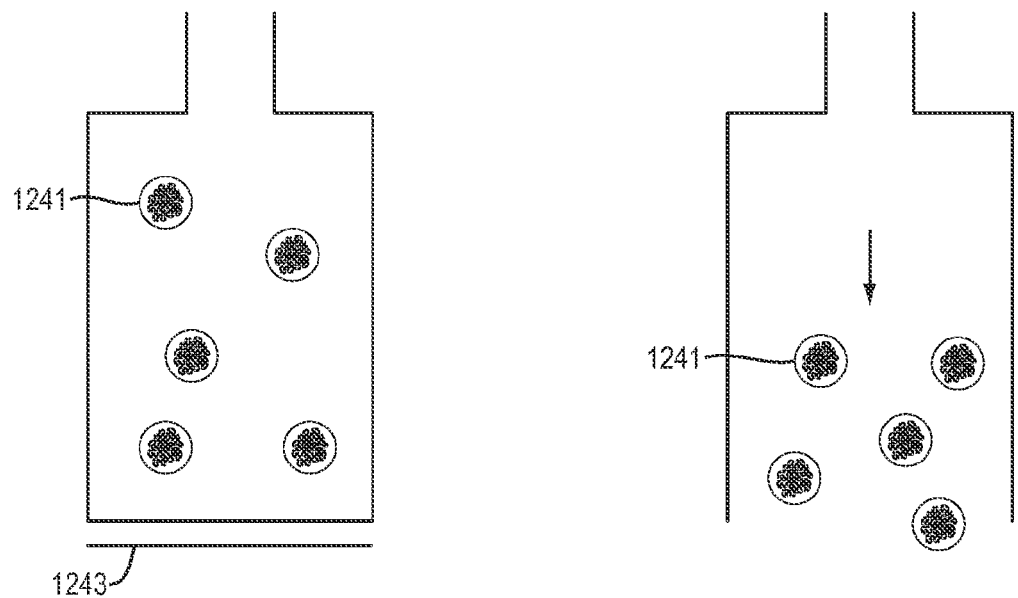
FIG. 12F
FIG. 12G

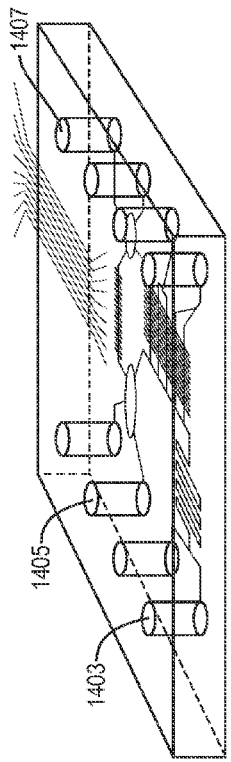
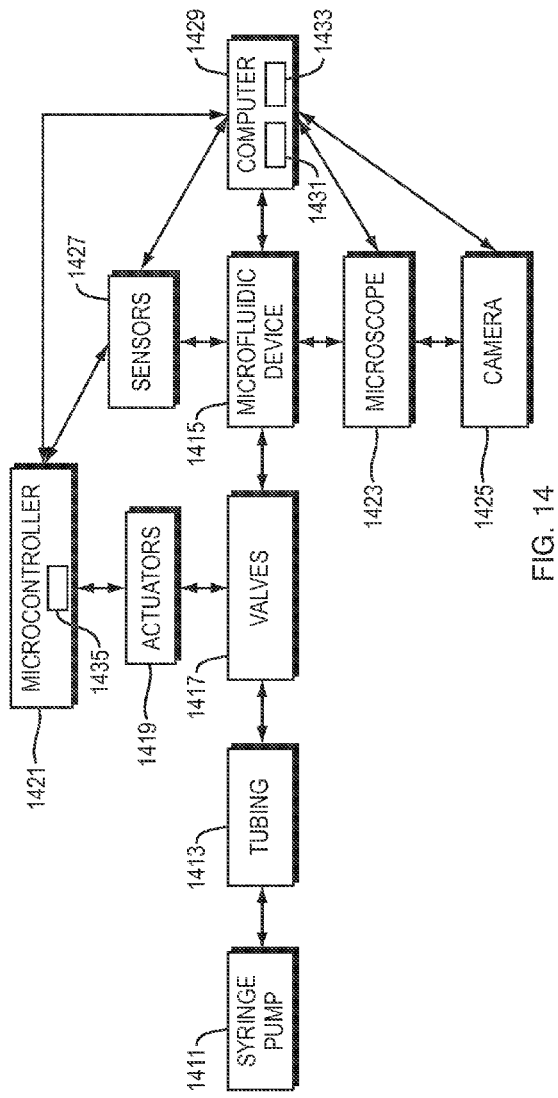

METHODS AND APPARATUS FOR TRANSPLANTATION OF NUCLEIC ACID MOLECULES

RELATED APPLICATIONS

This application is a non-provisional of, and claims the benefit of the filing date of, U.S. Provisional Application No. 61/860,626, filed Jul. 31, 2013, the entire disclosure of which is herein incorporated by reference.

STATEMENT REGARDING FEDERALLY SPONSORED RESEARCH OR DEVELOPMENT

This invention was made with Government support under Contract No. HR0011-12-1-0003 awarded by the Defense Advanced Research Projects Agency and under Grant No. AI098057 awarded by the National Institutes of Health. The Government has certain rights in the invention.

FIELD OF THE TECHNOLOGY

The present invention relates generally to microfluidics.

SUMMARY

In exemplary implementations, this invention mitigates a problem that occurs during conventional transfer of nucleic acids into a biological cell: The problem is that nucleic acids outside cells, extracted from an organism or synthesized from oligonucleotides, are fragile, and can be damaged by the shear forces that occur during fluid flow. Damage from shear forces can prevent (or reduce the likelihood of) a successful transfer. This problem is particularly acute when nucleic acids are large. For example, a large nucleic acid molecule with more than 100,000 base pairs tends to be more fragile, and more susceptible to damage from shear forces, than a smaller nucleic acid.

In exemplary implementations of this invention: (1) interaction between large nucleic acids and recipient cells occurs in a microfluidic chamber, shielded from shear forces; (2) the chemical environment in the chamber is controlled through fluidic methods; (3) parallelized processes are used for high throughput and multiplexed screening; and (4) a microscope is used for high spatiotemporal visualization of large DNA and cells during the transfer process.

In exemplary implementations, cells and buffers move gently into the microfluidic chamber (e.g., by diffusion). The gentle movement does not cause strong shear forces that would damage the contents of the chamber.

In exemplary implementations, transplantation of nucleic acids into cells occurs in microfluidic chambers. Buffers are moved into and out of the chamber to make the recipient cells competent (ready for transplantation) and to trigger transplantation. The contents of the chamber (e.g., isolated nucleic acids or "naked" nucleic acids) are shielded from shear forces that would ordinarily occur during pipetting, or shaking, or flow in a main flow channel of a microfluidic device.

In some cases, the microfluidic chamber is analogous to a little inlet with quiet waters that is connected to a flowing stream. In some cases, any fluid flow into, out of, or within the microfluidic chamber has a low Reynolds number (e.g., a Reynolds number less than 10). The turbulence and shear forces present in conventional methods are nonexistent or greatly reduced inside the microfluidic chamber. For example, in some cases (a) the chamber has only one orifice more than 180 nm across, which orifice is a permanent opening to a main channel, or (b) the chamber has a longitudinal axis that forms an angle of at least 45 degrees relative to direction of fluid flow in the main channel. As a result, the contents of the chamber are shielded from the shear forces that occur during fluid flow in the main channel. In this example, buffers move gently (e.g., by diffusion) into the chamber though the orifice.

In some cases, the orifice to the chamber is relatively small, compared to the chamber as a whole. For example, in some cases, (i) the orifice to the chamber subtends less than 3.14 steradians as seen from the center of a sphere, and (ii) the center of the sphere is located in the interior of the chamber. In some cases, the orifice to the chamber is smaller than the maximum chamber width, perpendicular to the longitudinal axis of the chamber. In some cases, the orifice to the chamber is smaller than 80% of the maximum chamber width, perpendicular to the longitudinal axis of the chamber.

In some cases, the chamber comprises a widened section of (or is connected at one or more inlets and outlets to) one or more microfluidic channels. Flow through the chamber (from inlet to outlet) temporarily ceases due to closing one or more valves. Transplantation occurs during a period in which the contents of the chamber (e.g., isolated nucleic acids) are shielded from shear forces that would occur during ordinary fluid flow in a flow channel.

In exemplary implementations, cells or buffers are loaded into microfluidic chambers by diffusion.

In other cases, centrifugation is used (in addition to diffusion) to load cells into the chambers. In other cases, a vacuum channel is used (in addition to diffusion) to load cells into the chambers. Suction from an adjacent vacuum channel draws fluid from the chambers (e.g., through one or more walls of the chambers), thereby causing a flow of cells and fluid into the chambers to replace the exiting fluid.

In some cases, cells or buffers are loaded into the chambers by dead-end loading. Fluid (e.g., air or liquid) exits the chambers (e.g., by diffusion though a wall of the chamber). Other fluid (in which the cells are suspended or buffers dissolved) flows into the chambers, to replace the fluid that is exiting.

During the vacuum suction or dead-end loading, the velocity of fluid flow into the chamber is much slower (e.g., less than a micron per second) than during ordinary flow in a main channel of the microfluidic device. This slow velocity tends to reduce shear forces.

In exemplary implementations, any fluid flow into the chamber is sufficiently gentle that it does not cause damage to isolated nucleic acids that would prevent successful transplantation.

In some implementations, lysis agents diffuse (or are dead-end loaded) into a microfluidic chamber. The lysis agents trigger lysis of one or more donor sources that are located inside the chamber. Then the lysis agents are removed from the chamber by diffusion or dead-end loading. Then recipient cells diffuse (or are dead-end loaded) into the chamber. Then transplantation agents diffuse (or are dead-end loaded) into the chamber to trigger transplantation of nucleic acids into the recipient cells. The transplantation occurs inside the chamber. The nucleic acids were, prior to the lysis, in the donor sources, such as biological cells or nuclei, or another source.

In some implementations, large nucleic acids with more than 100 kbp (kilo base pairs) are transplanted into recipient cells. In some cases, an entire genome or entire chromosome (such as a prokaryotic circular chromosome) is transplanted.

In illustrative implementations, neither the recipient cells, nor the donor sources, nor the nucleic acids are attached to a wall of the chamber prior to or during the transplantation.

In some cases: At all times during a process, no net fluid flow into or out of a set of one or more chambers occurs, except (i) net fluid flow, if any, that enters the set by diffusion (e.g., through a wall of a chamber) and exits the set in any way, or (ii) net fluid flow, if any, that exits the set by diffusion (e.g. through a wall of a chamber) and enters the set in any way. Also, at all times during the process, none of the chambers in the set, individually or together with other chambers in the set, form a fluidic loop, or if they do form a fluidic loop, no current flows in and around the loop. The process includes one or more of: (a) diffusing or dead-end loading lysis agents into a chamber to lyse donor cells; (b) removing the lysis agent from a chamber by diffusion or dead-end loading; (c) loading recipient cells into a chamber; (d) mixing, by at least diffusion, recipient cells and donor nucleic acid, which donor nucleic acid is from the lysed donor cells; and (e) diffusing or dead-end loading into a chamber divalent ions and crowding agents to trigger transplantation.

In a non-limiting example, recipient cells flow into a first chamber and donor cells flow into a second chamber. A lysis agent flows into an adjacent flow channel, and gently diffuses (e.g. through linking channels) into the second chamber to lyse the donor cells. Then the lysis agent is removed by flowing another buffer into an adjacent flow channel, so that the lysis buffer diffuses out of, and the other buffer diffuses into, the second chamber. Then the first and second chambers are fluidically connected (e.g., by opening valves), so that donor nucleic acids and recipient cells mix by diffusion. Then a buffer that makes the recipient cells competent (e.g., 0.1 M calcium chloride) flows into an adjacent flow channel, and gently diffuses (e.g., though linking channels) into the volume where the donor nucleic acids and recipient cells are located. Then a buffer that triggers transplantation flows into an adjacent flow channel, and gently diffuses (e.g., though linking channels) into the volume where the donor nucleic acids and recipient cells are located. In some cases, the transplantation buffer comprises (a) a crowding agent, such as polyethylene glycol, (b) other substances, such as Tris 10 mM, sodium chloride 250 mM, magnesium chloride 10 mM, or calcium chloride 15 mM, and (c) a growth medium such as 30% Spiroplasma broth 4 (SP4).

In illustrative implementations, hundreds or thousands of side chambers are arranged perpendicularly to flow channels. Physical and chemical gradients (such as concentration gradients or temperature gradients) are applied, so that different side chambers are at different points in the gradient.

For culturing cells (e.g., donor, recipient or transplanted cells), the microfluidic device delivers a steady stream of a nutrient-rich solution. Waste material produced by the cells, as well as cells that overgrow the chambers, flows away.

In exemplary implementations, the transplanted genetic material includes a gene for resistance to a particular antibiotic. After the cells recover from the transplantation, a solution containing the antibiotic is introduced to select for the transplanted cells and to eliminate recipient cells that did not receive the donor nucleic acids. The transplanted cells are then cultured until they overflow the chamber and enter a flow channel, from which they can be harvested as they flow out of the microfluidic device.

In exemplary implementations, an automated microscope with a camera is used to capture real-time visual data regarding events and objects inside the microfluidic device (such as loading of cells to chambers, lysis, transplantation, and cell culture). In addition, other sensors (e.g., embedded sensors) may be used to take real-time sensor readings of conditions (e.g., pH, temperature, pressure, or capacitance) within the microfluidic device.

In exemplary implementations, the microfluidic device includes valves, tubes, chambers and channels for delivering precise fluid volumes (and precise concentrations, reagent quantities, etc.) at precise times under gentle and controlled conditions. The microfluidic device includes parallel structures to facilitate high-throughput, parallel testing and procedures.

The description of the present invention in the Summary and Abstract sections hereof is just a summary. It is intended only to give a general introduction to some illustrative implementations of this invention. It does not describe all of the details of this invention. This invention may be implemented in many other ways. Likewise, the description of this invention in the Field of the Technology section is not limiting; instead it identifies, in a general, non-exclusive manner, a field of technology to which exemplary implementations of this invention generally relate.

BRIEF DESCRIPTION OF THE DRAWINGS

FIG. 3A shows an upside-down, exploded view of a microfluidic device that includes microfluidic channels in PDMS. FIG. 3B shows an exploded view of a microfluidic device that includes microfluidic channels in glass.

FIGS. 4A, 4B, 4C, 4D, 4E, 4F, 4G show a microfluidic chamber at different times during transplantation of nucleic acids.

FIG. 8A shows a large number of cells loaded into microchambers, using a vacuum channel to facilitate flow. FIG. 8B shows a smaller number of cells loaded into microchambers, without using a vacuum channel to facilitate flow.

FIG. 9A shows a microfluidic device that creates a concentration gradient between a low concentration channel and high concentration channel. FIGS. 9B and 9C show a "zoomed out" bottom view and "zoomed in" bottom view of this device, respectively. FIG. 9D shows a perspective view of this microfluidic structure for creating a concentration gradient.

FIG. 10A shows an example, in which increasing the concentration of a divalent ion tends to increase clustering of donor genetic material and recipient cells.

FIG. 10B shows an example, in which increasing concentration of a crowding agent tends to increase transplantation of genetic material and cell fusion. FIG. 10C shows examples of other gradients.

FIG. 11A shows a microfluidic device that includes multiple valves. FIGS. 11B and 11C show cross-sectional views in which a valve is open and closed, respectively.

FIGS. 12A and 12B show recipient cells and donor genetic material separated by a closed valve, and mixing after the valve is opened, respectively. FIG. 12C shows recipient cells and donor genetic material that are not mechanically compressed, while a valve is open. FIG. 12D shows recipient cells and donor genetic material that are mechanically compressed, while a valve is closed. FIG. 12E shows a microfluidic device with multiple, independently controlled regions. FIGS. 12F and 12G show cells while a valve is closed, and after the valve is opened to harvest them, respectively.

FIG. 13 shows an automated microscope and other sensors for real time observations and sensor readings regarding processes occurring with a microfluidic device.

FIG. 14 shows a high-level diagram of hardware components of a system for transplantation of nucleic acids.

Figure 1:
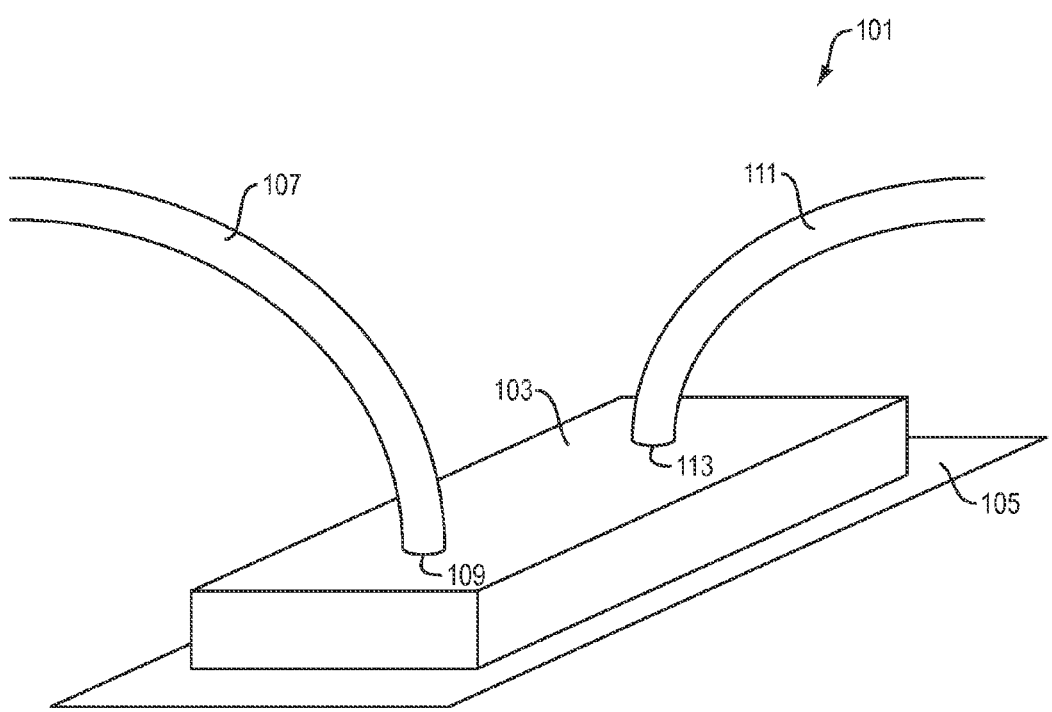
FIG. 1 shows a microfluidic device for transplantation of nucleic acids.

The above Figures show some illustrative implementations of this invention, or provide information that relates to those implementations. However, this invention may be implemented in many other ways.

DETAILED DESCRIPTION

In exemplary implementations of this invention, a microfluidic device is used for transplantation of nucleic acids into cells. In some cases, the nucleic acids that are transplanted are large nucleic acids ("LNAs").

In exemplary implementations, large nucleic acid transplantation (also called "genome transplantation" or "GT") occurs in a microfluidic device. The microfluidic device: (a) confines donor LNAs and recipient cells in controlled microenvironments with controlled geometries that encourage GT; (b) shelters LNAs from shear forces; (c) compresses LNAs and cells via mechanical pressures; (d) changes ambient buffer around the cells in seconds (optionally, without centrifugation); (e) applies chemical gradients and other physical gradients (e.g., temperature gradients) so that a parameter varies in a gradient over at least a portion of the microfluidic device; (f) is mounted to an automated microscope with a camera, such that visual images of donor cells, LNAs, recipient cells, and steps in transplantation are captured in real time.

In exemplary implementations, a microfluidic device includes features with various geometries and length scales, from microns to centimeters.

Fabrication of Microfluidic Device:

In exemplary implementations, soft lithography is used to fabricate a microfluidic device as follows: CAD software is used to design chrome photomasks. The chrome masks are then purchased from commercial vendors. Spin coating is used to deposit positive (e.g., phenolic resins)/negative (e.g., SU-8) photoresist onto silicon wafers. A mask aligner projects an image of the chrome mask onto the substrate to cure shielded/exposed regions of the photoresist layer, then resins are used to develop the resist. In some cases, the resist is baked before or after exposure. The soft lithography involves one or more of a wide range of subtractive and additive processes, combined to make devices with multiple layers. In one example: (1) Bosch deep reactive-ion etching (subtractive) is used to pattern shallow features (submicron to microns), such as chambers for cells and whole genomes; then (2) SU-8 (additive) is used to pattern deeper features (microns to tens of microns), such as channels that connect the chambers to inlets, outlets, and various fluidic modules.

In other implementations, excimer laser micromachining is used to fabricate a microfluidic device, as follows: CAD/CAM software generates toolpaths for the automated excimer stage. The excimer laser emits an energetic, pulsed UV beam (KrF 248 nm, ArF 193 nm) with a uniform profile, several centimeters in diameter. The excimer laser machines masks in stainless steel sheets, each on the order of 100 microns thick, or the masks in stainless steel or another material are obtained by other means. The masked beam is focused onto substrates such as borosilicate glass, silicon, polydimethylsiloxane (PDMS), polycarbonate, polyimide, and epoxies. The excimer laser ablates on the order of 100 nm depth per pulse and can achieve feature footprints with various shapes and sizes (microns to millimeters). In contrast to conventional soft lithography techniques, the excimer laser enables rapid design/build/test iteration of 2.5D devices in hard substrates.

In some implementations, a microfluidic device is assembled using polydimethylsiloxane (PDMS), as follows. PDMS structures are cast from the masters fabricated via soft lithography. To prevent adhesion between the cured PDMS and the silicon or glass master, the master is vapor coated in an evacuated vacuum chamber with (tridecafluoro-1,1,2,2-tetrahydrooctyl)trichlorosilane (TFOCS) for about 2 hours at room temperature, to silanize the surfaces. An elastomer base and a curing agent are mixed in a 5:1 to 20:1 ratio by mass. Air bubbles are removed with a vacuum pump or a centrifuge. The viscous PDMS is poured over the master. The PDMS cures on the master at 65° to 80° C. for about 12 hours, or at room temperature for at least 1 day. Then the microfluidic device is peeled from the master and left at room temperature.

In some implementations, microfluidic chambers and channels are recessed into PDMS slabs. If the PDMS layer is not thick enough to support stable interfaces with tubing, PDMS blocks are plasma bonded over inlet and outlet features. A coring tool punches inlet holes and outlet holes in the PDMS.

In other implementations, microfluidic chambers and channels are recessed into borosilicate glass layers (e.g., glass cover slips). In some cases, an excimer laser is used to create the recesses in the glass.

In exemplary implementations, the device components are bonded or joined together. In some cases, if the microfluidics device includes PDMS, oxygen plasma is used to bond textured PDMS to flat borosilicate cover slips or to bond textured cover slips to flat PDMS. Different types of plasma systems may be used. In one example: (a) substrates are placed onto a metal grid within a vacuum chamber; (b) a rotary vacuum pump evacuates the vacuum chamber for 1 minute; (c) the vacuum chamber is placed in a large microwave; and (d) the microwave is run at 30 percent power for 4 seconds. With these settings, the plasma sparks after about 2 seconds and glows purple. The surfaces are then adhered without introducing air bubbles, and are then baked at 80° C. for 10 minutes. In another example, borosilicate glass cover slips are cleaned, and then bonded together in a muffle furnace at 640° C. for several hours.

After parts of a microfluidic device are bonded with oxygen plasma, the surfaces carry residual negative charge. To passivate the surfaces (chemical modifications to prevent nonspecific adsorption of cells and genetic material to the microfluidic chambers), a solution is infused into the device. In one example, the passivating solution comprises 0.1 mg/mL poly-L-lysine (20 kDa) covalently grafted (grafting ratio 3.5) to polyethylene glycol (5 kDa) (PLL-g-PEG) in 10 mM HEPES buffer at pH 7.4. After the passivating solution is infused into the microfluidic device, the device is incubated at room temperature for 30 minutes. Then the device is washed with sterile water. Tubing driven by syringes, or pipettes, are used to load new buffers to the device. Before using any particular tubing, the particular tubing is sterilized with 70 percent ethanol and sterile water. It is desirable, after assembly and hydration of the microfluidic device, to use the microfluidic device as soon as possible. If a microfluidic device will not be used within 3 hours after the assembly and hydration, then the device is stored in a moist environment to prevent evaporation and dehydration.

Ingress and Egress:

In exemplary implementations, a syringe mounted on a syringe pump is used to infuse new buffers into a microfluidic device. Tubing (e.g., polyethylene or Tygon® tubing) connects the syringe to the microfluidic device. Blunt needles or Upchurch Scientific® fittings are used to connect the tubing to Luer-Lok or slip tip syringes. New buffers are infused into the microfluidic device at hundreds of microliters per hour. The total device volume is several microliters. To ensure that a previous buffer is flushed from the device, tens of microliters flow through the device over several minutes. Fluid flow passes through all regions of the main channel of the device, so that previous buffers do not remain in the device and do not contaminate subsequent buffers via diffusion.

In some cases, valves and other fluidic modules are used to store and infuse multiple buffers in series. In one example: (a) genome transplantation buffers are loaded into separate syringes; (b) the syringes are connected to a multi-port valve via tubing; (c) each respective tube is primed to purge air from the respective tube; and (d) the multi-port valve is connected to the microfluidic device with another tube.

In some cases, a tube connects an outlet port of the microfluidic device to a closed outlet container, to decrease the chance of contamination, or to save the buffer that flows through the device. In other cases, tubes and external valves or vacuums are used to create positive or negative pressure with microfluidic modules, such as PDMS valves to open/close regions of the device, or vacuum channels to pull water through the PDMS chambers and increase the local concentration of cells and genetic material.

Strain Construction:

In exemplary implementations, after transplantation, an antibiotic is used to select recipient cells that received donor genetic material, and to kill other cells. An antibiotic resistance gene is added to, or is naturally occurring in, the donor genetic material. After transplantation, an antibiotic, such as tetracycline or puromycin, is added to the growth medium. In some cases, a cytoplasmic fluorescent protein gene (such as mCherry) is added to the donor genetic material. In those cases, after the transplantation, the transplanted cells fluoresce, but other recipient cells which did not undergo transplantation (did not bring in the donor genetic material) do not fluoresce.

In some cases, steps are taken to prevent horizontal transfer of the antibiotics resistance gene from the donor cell to the recipient cell. In some cases, the steps comprise causing the recipient cell genome to lack restriction enzymes. In other cases, small molecules (such as mitomycin C) are added to inactivate the recipient genomes.

Preparation of Donor Cells and Recipient Cells:

In exemplary implementations, donor cells and recipient cells are cultured in liquid medium. In some cases, the donor genetic material is extracted from yeast nuclei or bacteria. If the donor genetic material is derived from yeast nuclei, the yeast nuclei are first isolated from spheroplasted yeast cells.

In exemplary implementations, donor and recipient cells are grown in liquid medium or grown on agar plates. A nutrient-containing growth medium (such as SP4, in the case of mycoplasmas) is used. The choice of growth medium depends on the cell species. In some cases, prior to use of the liquid growth medium, a stock solution that includes fetal bovine serum is stored at −80° C. or an agar plate is stored at 4° C. In some cases (e.g., some examples where the cells are mycoplasmas), the growth medium comprises: (a) Spiroplasma medium 4 (SP4), (b) SOB+serum+glucose (SSG), or (c) Media 243. The recipient cell medium that maximizes transplant yield does not in general maximize cell growth rate, and optimal growth media and optimal density of cells depends on the donor and recipient species. In some cases (e.g., some examples where the cells are mycoplasmas): (a) as the cell culture grows, the pH of solution decreases; and (b) the optimal density of cells occurs above pH 6, before the cells consume all the nutrients in the growth medium and revert to another physiological mode.

In exemplary implementations, donor and recipient cells are grown (separately) to an optimal density at 30° C. or 37° C. in an incubator. To measure cell density, a pH sensor measures the pH of the solution or a microscope (and optionally a camera) are used to visually measure the concentration of cells. As cell density increases, the optical density increases. In some cases, as cell density increases, the pH decreases from 7.5 to below 6.

In exemplary implementations, after the cells are grown, the cells are centrifuged and the supernatant is removed. Then the cells are washed in a buffered solution. In some cases, this buffered solution comprises (a) Tris plus sodium chloride (Tris NaCl), (b) Hanks balanced salt solution (HBSS), or (c) buffered saline (PBS). In some cases, the cells are resuspended in a smaller volume in order to concentrate the cells.

Microfluidic Workflow:

Microfluidic transplantation has numerous advantages unique to microfluidics, such as fast and precise control over physical and chemical conditions in the devices, and real time visualization with high spatiotemporal resolution.

In exemplary implementations, donor genetic material is transplanted into recipient cells in a microfluidic device. In some cases, the donor genetic material that is transplanted comprises large nucleic acids, and the transplantation comprises large nucleic acid transplantation.

In exemplary implementations, the transplantation process includes flowing a sequence of buffers through a microfluidic device.

In some implementations, one or more of the following are infused into the microfluidic device: (a) a buffered solution (such as Tris NaCl, HBSS, or PBS); (b) yeast nuclei with donor chromosomes, or donor cells, or another source of nucleic acids, in buffered solution; (c) a lysis buffer (such as sodium deoxycholate, sodium lauryl sarcosine, Triton X-100 detergent, IGEPAL CA-630, or another detergent); (d) a crowding agent (such as polyethylene glycol (PEG), dextran, or Ficoll® solution) for compacting donor genetic material (e.g. while washing donor cytoplasm from the microfluidic device); (e) recipient cells in a buffered solution (which solution includes a cell competence buffer, such as 0.1 M calcium chloride); (f) a transplantation buffer; (g) growth medium plus serum; or (h) growth medium plus serum plus antibiotic. In some cases, the transplantation buffer includes a crowding agent (such as PEG, dextran, or Ficoll®), a growth medium without serum, calcium chloride, and a buffered solution (such as Tris NaCl, HBSS, or PBS). In some cases, the transplantation buffer comprises one or more of the following: Tris 10 mM, sodium chloride 250 mM, magnesium chloride 10 mM, calcium chloride 15 mM, MW 8000 polyethylene glycol 5%, and 30% *Mycoplasma* growth medium such as SP4.

In exemplary implementations, the optimal lysis buffer depends on the donor species. For example, in some cases, enzymes are used to digest a cell wall and form spheroplasts, and then detergents or abrupt osmotic changes are used to lyse the cells.

In exemplary implementations, it is desirable that cells do not experience abrupt osmotic pressure changes when entering the microfluidic device. To achieve this goal, a buffered solution (such as Tris NaCl, HBSS, or PBS) is infused to the device, after passivating surfaces of the microfluidic device and before infusing the cells.

In exemplary implementations, cells and donor genetic material that are located in the side chambers do not experience flows as the ambient buffer around them is changed.

In exemplary implementations, the yeast nuclei or donor cells are lysed with lysis buffer to extract chromosomes. The lysis buffer composition depends on the source of the donor chromosome. In some cases, crowding agents are added to the lysis buffer, to confine the large donor chromosomes to certain device regions as the smaller cytoplasmic molecules and residual membrane fragments diffuse from the chambers then exit the device. The lysis buffer is then purged from the microfluidic device with a buffered solution (such as Tris NaCl, HBSS, or PBS), to prevent lysis of the recipient cells.

In exemplary implementations, recipient cells are loaded to the microfluidic device via diffusion (and, in some cases, the cells are concentrated via centrifugation or vacuum). Next, a buffer is infused to make the recipient cells chemically competent to receive donor genetic material. The microfluidic device is incubated on ice for about 30 minutes, then the transplantation buffer is added and the device is incubated again at room temperature or in an incubator. The optimal concentration of crowding agent, and incubation temperature and duration, depend on the recipient cell type. In one case, the microfluidic device is incubated with 5% polyethylene glycol buffer at 37° C. for about 80 minutes. After incubation with the transplantation buffer, growth medium is infused without antibiotic, to allow the cells some time to recover after transplantation and to express the antibiotics resistance genes.

For example, in some cases, SP4 medium with serum without tetracycline is infused as the devices incubate at 37° C. for about 90 minutes. After the cells recover, the growth medium that includes an antibiotic, such as tetracycline or puromycin, is infused. The growth medium enters the device at 37° C. The devices remains at 37° C. and growth medium continues to be infused for tens of hours, so the transplanted cells grow within the microfluidic devices. When one buffer is exchanged for another, care is taken so that air bubbles are not introduced into the tubing or devices.

Different device geometries involve different buffer sequences. For example, in some cases, donor genetic material and recipient cells are loaded in buffered solution to different microfluidic regions, separated by a closed valve. The cells and donor genetic material are prepared in parallel. Then a valve is opened to mix the cells and donor genetic material. Then additional buffers are infused to continue the transplantation process.

Cell Harvesting:

In some implementations, cells are harvested from the microfluidic device after transplantation occurs, as follows: A syringe pump causes fresh growth medium plus antibiotics to flow through the device (e.g., at a fluid flow rate of 400 uL/hr). The syringe pump is connected to the inlet port in the PDMS via a tube. Another piece of tubing connects the outlet port in the PDMS block to a port, which port is into a container outside the device. The growth medium that passes through the device is collected in an outlet container. Cells overgrow the microfluidic chambers or regions. The entire system is closed to prevent contamination by bacteria or spores in the atmosphere outside the sterilized microfluidic system.

Only transplanted cells have the gene that confers resistance to the antibiotic in the growth medium, so transplanted cells grow in the side chambers, while the background of recipient cells that did not receive donor genetic material do not grow in the chambers. The transplanted cells grow to fill the chambers and then overgrow the chambers into the main channel. Then, flow in the main channel washes the cells out of the device and into the outlet container, where the transplanted cells inoculate a liquid culture. This harvests transplanted cells in a single outlet container.

Thus, in some cases, a clonal population of donor cells leads to a clonal population of transplanted cells. In some cases, even a single transplanted cell grows into a self-replicating colony of transplanted cells.

In some cases, valves are opened to flow the transplanted cells from the microfluidic device; or fast buffer exchange and osmotic pressure gradients are used to pull cells from microfluidic chambers or regions.

Verification:

In some implementations, steps are taken to confirm that the harvested cells are transplanted cells. In some cases, these steps include: (a) checking for phenotypic markers, such as expression of enzymes or fluorescent proteins and antibiotic resistance proteins; (b) plating the cells on agar to check the colony morphology, as different species have different colony morphologies; and (c) performing polymerase chain reaction (PCR) to confirm transplantation of the desired donor genetic material (e.g., a large nucleic acid), rather than just horizontal transfer of the donor antibiotic resistance genes used to select. In some cases, an array of primers for sequences specific to either the donor or the recipient strain is used to confirm that the harvested cells do not have chimeric genomes with both donor and recipient sequences. In some cases, a recipient strain with a plasmid is used to verify transplanted cells, in that (i) the donor cells lack the recipient plasmid, (ii) recipient cells lack the donor genetic material, and (iii) transplanted cells have both the donor genetic material and the recipient plasmid.

Further Details:

Turning now to the drawings, FIG. 1 shows a microfluidic device 101 for transplantation of nucleic acids. The device comprises a polydimethylsiloxane (PDMS) slab 103 and a glass (e.g., borosilicate) cover slip 105. Microfluidic channels and chambers are recessed in either the PDMS slab 103 or the glass cover slip 105. During assembly of the microfluidic device, surfaces of the PDMS slab 103 and glass cover slip 105 are activated with plasma oxygen and then bonded together to seal the microfluidic channels and compartments. A tube 107 interfaces with an inlet 109 in the PDMS slab 103. Another tube 111 interfaces with an outlet 113 in the PDMS slab 103. An external syringe pump is used to pump fluid through the device.

Figure 2D:
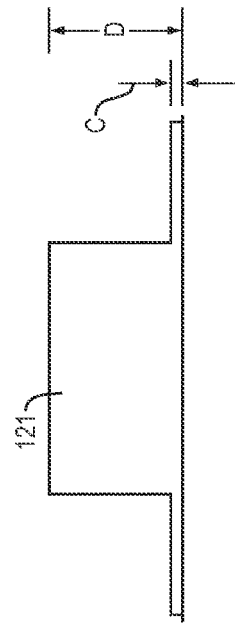
FIGS. 2B, 2C and 2D show a "zoomed out" bottom view, "zoomed in" bottom view, and cross-sectional side view, respectively, of this device.
Figure 2C:
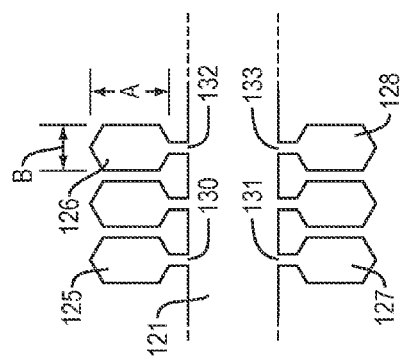
Figure 2A:
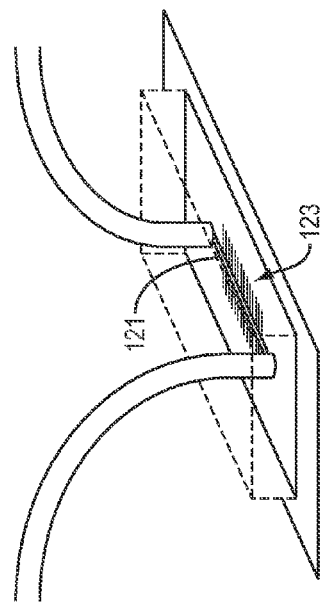
FIG. 2A shows part of the interior of the same device.
Figure 2B:
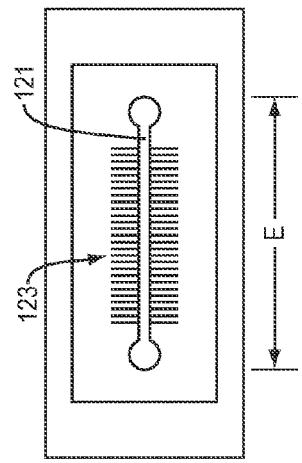

FIG. 2A shows part of the interior of the same microfluidic device. FIGS. 2B, 2C and 2D show a "zoomed out" bottom view, "zoomed in" bottom view, and cross-sectional side view, respectively, of this device.

In the example shown in FIGS. 1 and 2A-2D, a main channel 121 extends from the inlet 109 to outlet 113. Hundreds to thousands of microfluidic chambers 123 connect to the main channel 121. Each of these microfluidic chambers (e.g., 125, 126, 127, 128) has an opening (e.g., 130, 131, 132, 133) to the main channel 121, and is otherwise a closed surface, at least at the scale of a recipient cell or nucleic acid. Thus, an intact recipient cell or nucleic acid may enter or exit each chamber only through the opening to the main channel. (At a smaller scale, the walls of the chamber may be permeable, allowing smaller molecules such as water and air to pass through the walls of the chambers). Fluid flow in the main channel transports buffers, donor genetic sources (e.g., donor bacteria or yeast nuclei with yeast centromeric plasmids), and recipient cells. This flow is perpendicular to the chamber entrances. Molecules diffuse from the main channel into the chambers, and vice versa. Since the chambers are only tens of microns long, diffusive buffer exchange equilibrates the chambers with the main channel in seconds.

In the example shown in FIGS. 1 and 2A-2D: (1) the length A and width B of a microfluidic chamber are 20 microns and 15 microns, respectively; (2) the depth C of a microfluidic chamber is between 200 nm and 3 microns deep; (3) the depth D of the main channel is 30 microns; and (4) the length E of the main channel is 3 cm. However, the size and shape of the main channels and side chambers varies in exemplary implementations, and are not limited to the example shapes and dimensions described above.

In exemplary implementations, the microfluidic channels and chambers may be recessed in a variety of different materials. FIGS. 3A and 3B each show an exploded view of a microfluidic device. In FIG. 3A, the view is upside-down. In FIG. 3A, microfluidic channels and chambers 301 are recessed in a PDMS block 303, and a borosilicate glass layer 305 has a smooth surface. In FIG. 3B, microfluidic channels and chambers 311 are recessed in a borosilicate glass layer 313, and a PDMS block 315 has a smooth surface.

Figure 3C:
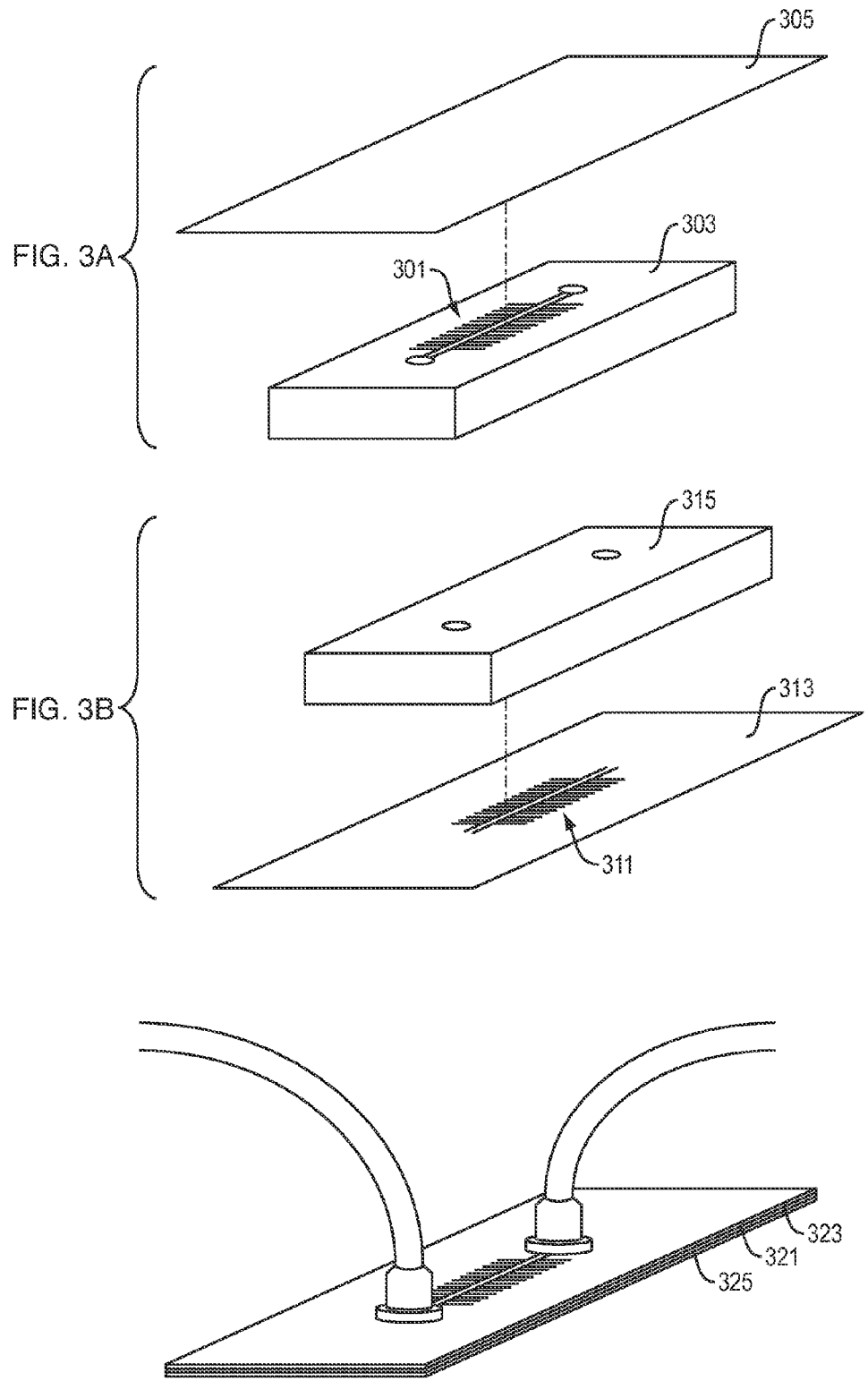
FIG. 3C shows a microfluidic device that includes two glass cover slips, with a layer between the cover slips.

FIG. 3C shows an alternative configuration of a microfluidic device, in which a PDMS block is not used. Instead, a middle layer of material 321 is sandwiched between two glass layers 323, 325. The microfluidic channels and chambers may be recessed into one or both of the glass layers or may be recessed into the middle layer.

In some cases, the middle layer of material 321 comprises tape or a silicon layer.

FIGS. 4A, 4B, 4C, 4D, 4E, 4F, 4G show a microfluidic chamber 401 at different times during transplantation of nucleic acids. In FIG. 4A, a biological container 403 (e.g., a bacterium or yeast nucleus) holds donor genetic material 405. In FIG. 4B, the cell membrane and nucleus of the cell have been lysed, so that donor genetic material 405 is extracted from the outer cell membrane and any nuclear membrane. In FIG. 4C, recipient cells (e.g., 407) have been loaded into the chamber, so that the donor genetic material 405 and recipient cells are in close proximity. In FIG. 4D, divalent ions (e.g., 409) have diffused into the chamber, and the donor genetic material and recipient cells have clustered together. In FIG. 4E, crowding agent molecules (e.g., 411) have also diffused into the chambers, causing donor genetic material to be transferred inside a recipient cell. In FIG. 4F, cells (e.g., 413,415) are recovering. In FIG. 4G, antibiotics have diffused into the chamber, selectively killing cells in which the donor genetic material is absent, but not killing cells in which the donor genetic material is present. A colony of transplanted cells (e.g., 417) containing the donor genetic material grows in the chamber, as nutrients diffuse into the chamber.

Figure 5A:
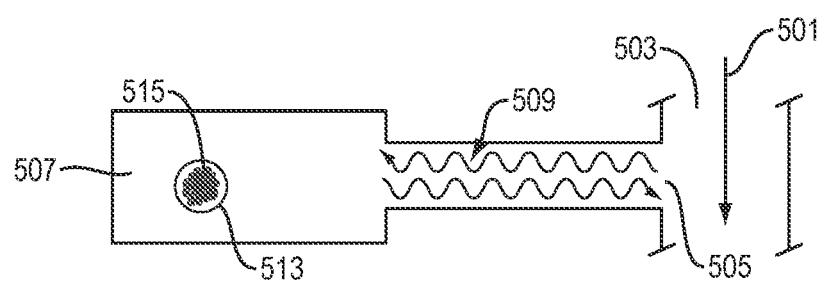
FIGS. 5A and 5B show a donor cell in a microfluidic chamber, before lysis and after lysis, respectively.
Figure 5B:
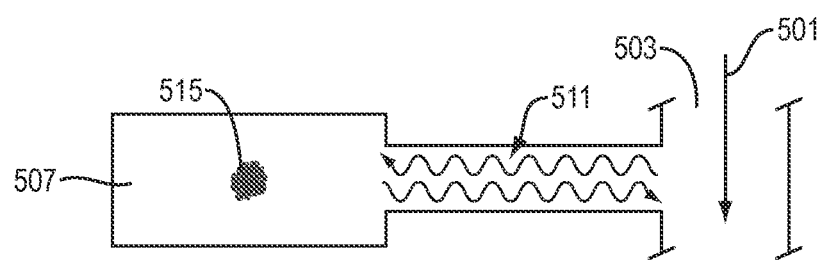
Figure 5C:
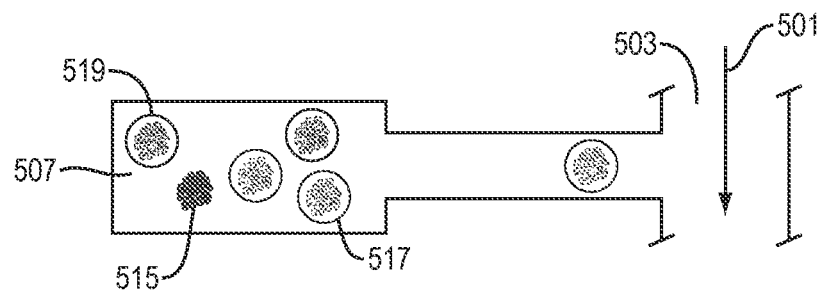
FIG. 5C shows recipient cells and donor genetic material, in a microfluidic chamber.
Figure 6A:
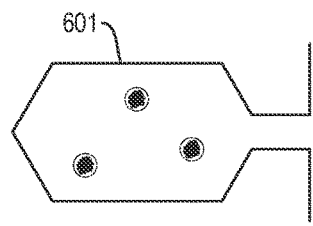
FIGS. 6A, 6B, 6C, 6D, 6E, 6F, 6G show different examples of sizes and shapes of microfluidic chambers.
Figure 6B:
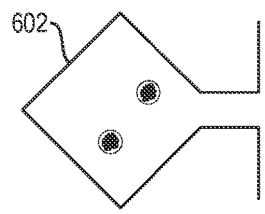
Figure 6C:
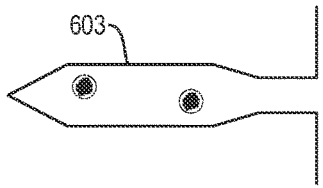
Figure 6D:
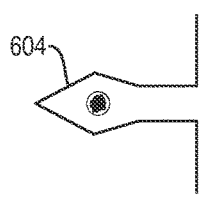
Figure 6E:
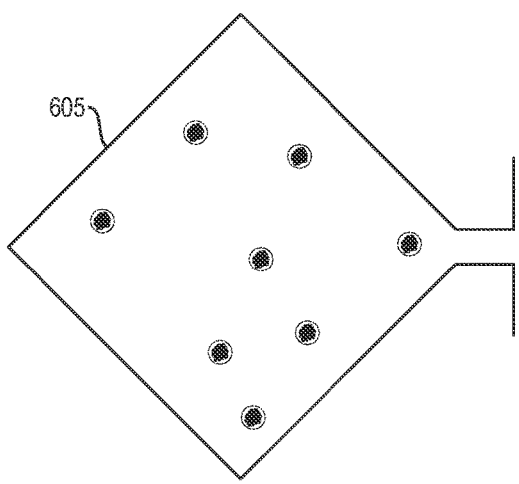
Figure 6F:
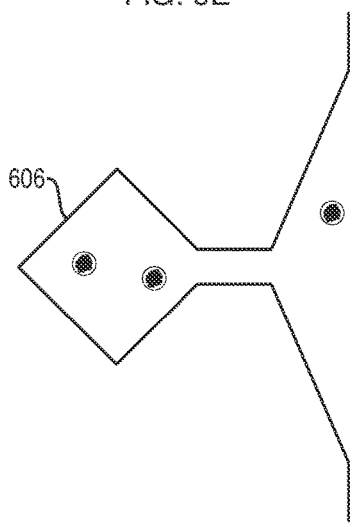
Figure 6G:
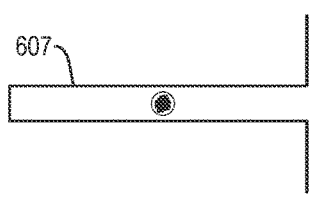

FIGS. 5A and 5B show a donor cell in a microfluidic chamber, before lysis and after lysis, respectively. In the example shown in these Figures, flow 501 in the main channel 503 brings buffers to the entrance 505 of the microfluidic chamber 507. Diffusive buffer exchange 509, 511 occurs between the microfluidic chamber 507 and the main channel 503, such that newly introduced buffers in the main channel equilibrate with the chamber in seconds. In FIG. 5A, an intact donor cell 513 holds donor genetic material 515. In FIG. 5B, the donor cell has been lysed by detergents or other lysing agents that diffused into the chamber. The donor genetic material 515 is in the microfluidic chamber 507, and thus is protected from shear forces that occur due to flow in the main channel 503. In FIG. 5C, recipient cells (e.g. 517, 519) have been loaded into the chamber.

In some implementations, valves are used to harvest particular regions of the device, so that multiple separate transplantation procedures may be run in parallel.

Here is an example of how donor genetic material is transplanted into recipient cells, in an illustrative embodiment of this invention:

In this example, a microfluidic device achieves fast physical and chemical control over donor genetic material and recipient cells, while protecting the genetic material and recipient cells from shear forces by positioning them in microfluidic side chambers. The side chambers create a gentle and controlled environment (shielded from shear forces) in which transplantation of nucleic acids occurs.

In this example, donor genome sources include bacteria or yeast nuclei. Cells are grown in liquid medium in a separate container, then the cells are concentrated 10 fold and resuspended in a suitable buffer such as 10 mM Tris at pH 6.5 plus 250 mM NaCl. The cells are then pipetted into a 1 mL BD syringe. Polyethylene tubing is connected to the syringe via a blunt needle. The tubing is connected to a PDMS block 103, then the donor genome sources (e.g., bacteria or yeast nuclei) are infused into the microfluidic device 101. The donor genome sources enter the main channel 121 of the microfluidic device. Next, flow is temporarily stopped in the main channel. This temporary cessation of flow in the main channel may be achieved by, among other things: (a) using one or more syringes to equilibrate pressures in the microfluidic device, (b) disconnecting one or more syringes and taping over the inlet and outlet, or (c) closing one or more valves.

In this example, donor genome sources are loaded into (move into) the side chambers 123 from the main channel 121. This movement may occur by diffusion, over a period of time lasting tens of minutes. Alternatively, the microfluidic device is centrifuged to increase the concentration of cells near the chambers, to achieve sufficient loading rates in a few minutes. Alternatively, other microfluidic modules, such as vacuum channels integrated into the device, can accelerate the loading process without centrifugation.

In this example, a microscope is used to check the loading rate of the donor genome sources in the side chambers. With the microscope, a donor genome can be directly visually observed. In this example, direct visualization via microscopy is also used in other contexts, such as to evaluate the extent of lysis, to monitor the progress of the transplantation, and to verify transplantation. (If a centrifuge is used to load cells into chambers, then the microfluidic device may be dismounted from the microscope in order to centrifuge the device.)

In this example, donor genetic sources are lysed with detergents or other lysis agents. To infuse the lysis buffer, a syringe is filled with the lysis buffer solution, and a new segment of tubing is connected to the syringe via a blunt needle. The tubing is connected to the device, and a syringe pump is used to infuse the lysis buffer through the main channel. The lysis buffer flows along the main channel, then the lysis buffer diffusively equilibrates with the buffer in the side chambers in seconds. The combined volume of the side chambers is much smaller than the volume of the main channel. More lysis buffer is infused, so the microfluidic device fills with lysis buffer. In seconds, lysis buffer surrounds the donor genome sources, even though the interior of the chamber is shielded from the flow that occurs in the main channel.

In this example, the lysis buffer is then washed away with a Tris NaCl buffer. The syringe and inlet tubing are disconnected, and a new syringe plus tubing is connected. Care is taken to introduce no air bubbles to the device. A syringe pump infuses the Tris NaCl buffer into the microfluidic device along the main channel, then the Tris NaCl buffer diffuses from the main channel into the side chambers. At the same time, the lysis buffer diffuses out of the side chambers and into the main channel, and then flows out of the device. Alternatively, a separate reservoir for each of the different buffers (e.g., lysing buffer and Tris NaCl buffer) may each be connected by separate tubing to a valve with multiple ports, so that tubing interfaces do not need to be changed during a transplantation procedure.

In this example, recipient cells are then loaded into the side chambers in an appropriate buffer. A series of buffer exchanges (similar to the buffer exchange described above) occurs. A buffer with divalent ions is infused, to chemically make the recipient cells competent (ready for transplantation) and to cluster the genomes and cells. Then, a buffer with a crowding agent is infused to facilitate the transplantation of donor genetic material into the recipient cells.

In this example, a nutrient-rich media is then infused and the crowding agent is washed away. The recipient cells recover in the rich media. After another incubation period, antibiotic is added to the growth medium to select transplanted cells over the background of recipient cells that have not received donor genetic material. Outlet tubing from the device is connected to a container in order to collect growth medium that flows through the device. If a transplanted cell grows within the device, within several generations it grows out of the side chambers, flows through the main channel and the outlet tubing, and inoculates the liquid growth medium in the outlet container. This simple device harvests transplanted cells together in a single outlet container. A clonal population of donor cells leads to a clonal population of transplanted cells, and even a single transplanted cell may grow into a self-replicating colony of transplanted cells.

FIGS. 6A, 6B, 6C, 6D, 6E, 6F, 6G show different examples of sizes and shapes of microfluidic chambers 601, 602, 603, 604, 605, 606, 607.

Figure 7D:
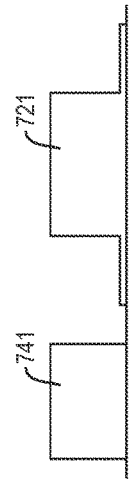
FIGS. 7B, 7C and 7D show a "zoomed out" bottom view, "zoomed in" bottom view, and cross-sectional side view of this device, respectively.
Figure 7C:
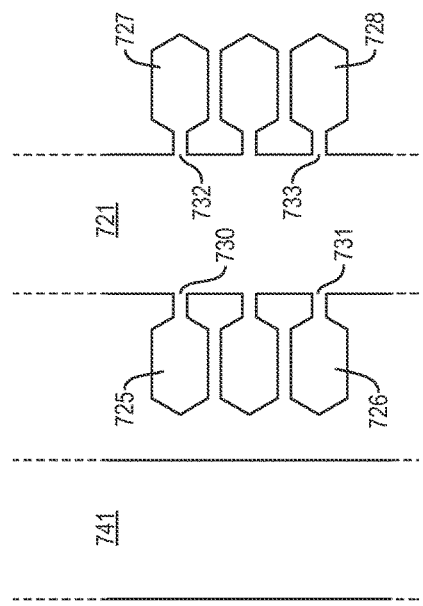
Figure 7A:
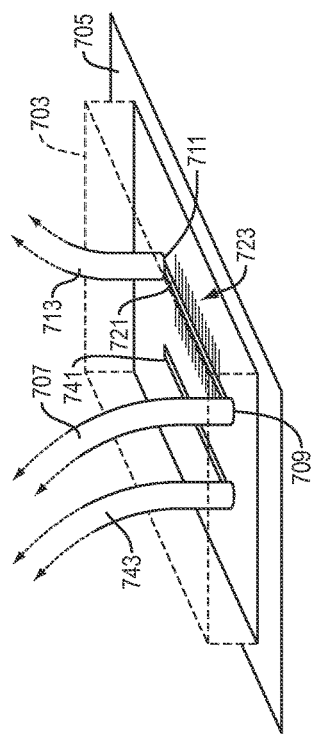
FIG. 7A shows a microfluidic device, including a vacuum channel, main channel and side channels.
Figure 7B:
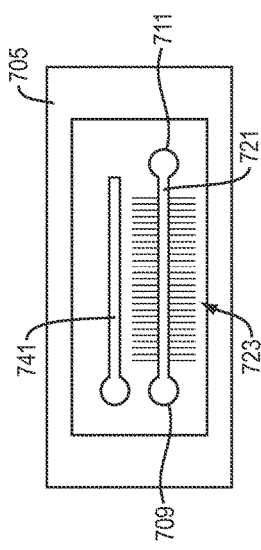

FIG. 7A shows a microfluidic device, including a vacuum channel, main channel and side channels. FIGS. 7B, 7C and 7D show a "zoomed out" bottom view, "zoomed in" bottom view, and cross-sectional side view of this device, respectively.

A vacuum channel 741 is connected to tubing 743 that is in turn connected to a vacuum pump. Otherwise, the configuration is similar to the example shown in FIG. 1: a microfluidic device comprises a PDMS slab 703 and a borosilicate glass cover slip 705. Microfluidic channels and chambers are recessed in either the PDMS slab 703 or the glass cover slip 105. Fluids may be infused through an intake tube 707 through an inlet 709, and exit through an outlet 711 and then outlet tube 713. A main channel 721 extends from an inlet 709 to outlet 711. Microfluidic chambers 723 connect to the main channel 121. Each of these microfluidic chambers (e.g., 725, 726, 727, 728) has an opening (e.g., 730, 731, 732, 733) to the main channel 721.

In the example shown in FIGS. 7A-7D, the vacuum channel 741 is used to, among other things, facilitate loading of donor cells or recipient cells into the side chambers. The PDMS block is permeable to water and certain other molecules smaller than nucleic acids. The pressure difference between the side chambers and the vacuum tube induces a gentle flow of fluid from the side chambers through the PDMS into the vacuum tube. (For example, this gentle flow rate may be less than a micron per minute, compared to a flow rate of hundreds of microns per second in the main channel). However, the cells and nucleic acids do not pass through the permeable PDMS block, and are trapped in the side chambers. This vacuum-induced loading can speed up loading of cells into the side chambers.

In order to load cells into side chambers, either centrifuging, a vacuum channel or diffusion may be used. However, vacuum loading and centrifuging are faster than diffusion loading and achieve higher concentrations of cells in the side chambers. Vacuum loading has an advantage over centrifuging: Vacuum loading does not require dismounting the microfluidic device from a microscope and placing it in a centrifuge.

Figures 8A, 8B:
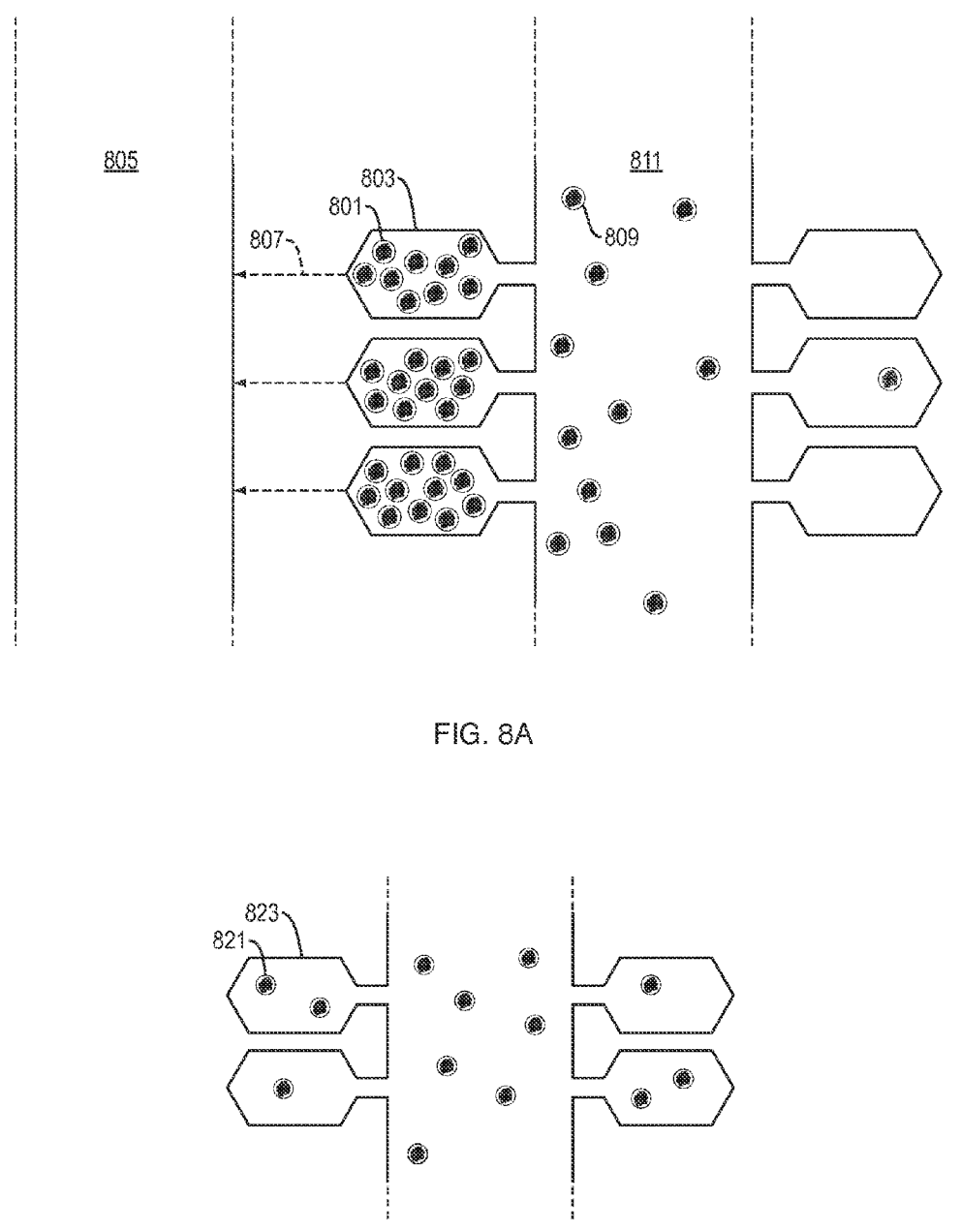

FIG. 8A shows a large number of cells (e.g., 801) loaded into microfluidic side chambers (e.g., 803), by using a vacuum in a vacuum channel 805. The vacuum causes a gentle flow (e.g., 807) of fluid from the side chambers (e.g., 803) to the vacuum channel. This gentle flow is induced by the pressure difference between the vacuum channel and the side chambers, and tends to draw cells (e.g., 809) from the main channel 811 into the side chambers. A microscope may be used to monitor the concentration of cells with a microscope, to achieve high control over the concentrations of cells and large molecules.

FIG. 8B shows a smaller number of cells (e.g., 821) loaded into side microchambers (e.g. 823), without using a vacuum channel to facilitate flow.

In exemplary implementations, a microfluidic device conducts parallelized searches through complex, multidimensional parameter spaces. For example, the device can be used to establish concentration gradients between parallel reservoirs, to test many chemical concentrations in parallel. For example, the yield of transplanted cells increases to a maximum as the concentration of crowding agent increases to an optimal concentration, and then decreases as the crowding agent concentration continues to increase. The location of this optimal concentration depends on the bacterial species involved in the transplantation procedure. Therefore, chemical gradients can be used to determine optimal transplantation conditions.

FIG. 9A shows a microfluidic device that creates a concentration gradient between a low concentration channel and high concentration channel. FIGS. 9B and 9C show a "zoomed out" bottom view and "zoomed in" bottom view of this device, respectively. A low concentration solution flows through a first channel 951 and a high concentration solution flows through a second channel 952. A set of microfluidic linking channels (e.g., 901) connect the first and second channels. Tens to thousands of microfluidic side chambers (e.g., 911, 913, 915) connect to each of these linking channels. A chemical concentration gradient is created along the length of the linking channels. Thus, different side chambers have different concentration solutions, depending on their position along a linking channel.

Optionally, each side chamber (e.g. 911, 913, 915) is attached to a separate outlet tube (e.g., 921, 923, 925) controlled by a separate valve or valve port (e.g., 931, 933, 935). Opening such a valve allows cells grown in a particular chamber to be harvested. Thus, cells that are affected by different concentrations can be harvested separately.

FIG. 9D shows another example of a microfluidic structure for creating a concentration gradient. In FIG. 9D, a linking channel 964 connects a low concentration channel 961 and a high concentration channel 962. Side chambers (e.g., 963) are connected to the linking channel 964. The concentration gradient varies along the length of the linking channel 964. Thus, the concentration at any particular side chamber depends on that chamber's position on the linking channel.

FIG. 10A shows an example, in which increasing the concentration of a divalent ion (e.g., 1001, 1003) tends to increase clustering of donor genetic material 1005 and recipient cells 1007. FIG. 10B shows an example, in which increasing concentration of a crowding agent (e.g., 1011, 1013) tends to increase transplantation of genetic material and cell fusion.

FIG. 10C shows examples of other gradients that may be created, using a configuration shown in FIGS. 9A-9D. For example, the gradient may be a chemical gradient such as a gradient in concentration of a growth media component 1021 or of a genetic compaction agent 1023. Or, for example, the gradient may be a physical gradient such as a gradient in transplantation temperature 1025 or growth temperature 1027. For example, the transplantation temperature may be a temperature at any step during a transplantation process, including a heat shock step.

FIG. 11A shows a microfluidic device 1100 that includes five valves: a first valve 1101, a second valve 1111, a third valve 1121, a fourth valve, 1131, and a fifth valve 1141.

The first valve 1101 allows recipient cells and donor genetic material to enter the microfluidic device. When open, the first valve 1101 allows donor genetic material to flow through channel 1103 to a first chamber 1105, and allows recipient cells to flow through another channel 1107 to a second chamber 1109.

The second valve 1111 allows buffers to reach the first chamber 1105 (where, at some times, donor genetic material is present). When open, the second valve 1111 allows a buffer solution to flow through channel 1113. Channel 1113 is connected to the first chamber 105 by a first set of linking channels (e.g., 1115) or by a continuous, shallow slit (too shallow to allow the passage of large DNA and cells, but deep enough to allow the passage of small molecules).

The third valve 1121 allows buffers to reach the second chamber 1109 (where, at some times, recipient cells are present). When open, the third valve 1121 allows a buffer solution to flow through channel 1123. Channel 1123 is connected to the second chamber 109 by a second set of linking channels (e.g., 1125) or by a continuous, shallow slit (too shallow to allow the passage of large DNA and cells, but deep enough to allow the passage of small molecules).

The fourth valve 1131 can used to open or shut outlet channel 1133 and outlet channel 1135.

The fifth valve 1141 allows items (e.g., donor genetic material and recipient cells) in the first and second chambers to mix. The first chamber 1105 and second chamber 1109 are connected to each other by a central set of linking channels (e.g., 1144), partitioned by blocks (e.g., 1143) to prevent the collapse of valve 1141. Opening or closing the fifth valve 1141 has the effect of opening and shutting this central set of linking channels (e.g., 1144). When the fifth valve 1141 is open, donor genetic material and recipient cells in the first and second chambers mix.

Optionally, the second valve 1111 also controls flow in outlet channel 1117, and the third valve 1121 also controls flow in outlet channel 1124.

An advantage of the configuration shown in FIG. 11A is that, at any time, the inlet valves and outlet valves may be closed, allowing items in the interior of the microfluidic device to gently mix by diffusion at a time when they are not experiencing the shear forces associated with fluid flow through the device from an inlet to an outlet.

The following example illustrates this advantage. In this example, fluid flow moves donor cells into the first chamber 1105 and moves recipient cells into the second chamber 1109. Then valves 1101, 1131 are closed, so that flow through the first chamber 1105 stops. Then valve 1111 opens, and a lysis buffer flows through channel 1113, then gently diffuses through the first set of linking channels (e.g., 1115) to the first chamber 1105. The lysis buffer then lyses the donor cells at a time when there is no flow through the first chamber 1105.

In this example, valve 1111 then opens, and another buffer flows into channel 1113, in order to remove the lysis buffer. The lysis buffer diffuses (from the first chamber 1105 to channel 1113) through the first set of linking channels (e.g., 1115). The other buffer diffuses (from channel 1113 to the first chamber 1105) through the first set of linking channels (e.g., 1115). This is accomplished at a time that there is no flow through the first chamber 1105. Then valve 1141 is opened so that isolated nucleic acids in the first chamber 1105 and the recipient cells in the second chamber 1109 mix by gentle diffusion through the central set of linking channels (e.g. 1144). Then divalent ions and crowding agents gently diffuse through the first set of linking channels (e.g., 1115) or the second set of linking channels (e.g., 1125) in order to induce clustering and transplantation of the donor genetic material into the recipient cells.

Thus, in this example, at various times (including during lysis and transplantation), the donor cells, donor genetic material, and recipient cells are protected from the shear forces that would be associated with flow through the first and second chambers 1105, 1109 from an inlet to an outlet.

FIGS. 11B and 11C show cross-sectional views in which a valve is open and closed, respectively. In both of these Figures, the valve is part of a multi-layered structure which includes a first PDMS layer 1161, a valve control line 1163, a second PDMS layer 1165, and a glass layer 1167. A channel 1169 is recessed into the second PDMS layer 1165. When the valve is open, channel 1169 is open. When the valve is closed, channel 1169 is closed. The position of the valve (open or closed) is controlled by controlling pressure of fluid in the valve control line 1163.

FIG. 12A shows recipient cells (e.g., 1201) and donor genetic material (e.g., 1203) separated by a closed valve 1205. FIG. 12B shows recipient cells (e.g., 1207) and donor genetic material (e.g., 1209) mixing after the valve is opened. FIG. 12C shows recipient cells (e.g., 1211) and donor genetic material 1213 that are not mechanically compressed, while a valve 1215 is open. FIG. 12D shows donor genetic material 1221 that is mechanically compressed, together with recipient cells, while a valve 1225 is closed.

FIG. 12E shows a microfluidic device with multiple, independently controlled regions (e.g., regions 1231, 1233).

At the end of a transplantation procedure (or after the transplanted cells have recovered and been selectively cultured), valves can be opened at the end of chambers, so that cells flow from the chambers. FIGS. 12F and 12G show cells (e.g., 1241) while a valve 1243 is closed, and after the valve is opened to harvest them, respectively.

In exemplary implementations, a microscope and light source are used for real-time observation of steps that occur in a microfluidic device in a transplantation procedure, including (1) preparation of donor cells and recipient cells, (2) lysis of donor cells, (3) clustering of recipient cells and genetic material, (4) transplantation, (5) subsequent cell culture of genetically modified cells, and (6) buffer infusion at any point in the process. The microscope and microfluidic device may be attached to each other, or one of them may support or be mounted on the other. The microscope may be automated, such that it automatically captures images. In addition, other sensors (such as thermometers, pH sensors, other chemical sensors, flow meters, pressure sensors, or capacitive sensors) may be embedded in, or attached to, the microfluidic device.

FIG. 13 shows an automated microscope 1401 and other sensors (e.g. 1403, 1405, 1407), for real time observations and sensor readings regarding processes occurring with a microfluidic device 1400. Optionally, the microscope 1401 is self-actuated for translating itself to different positions, such that it can observe all portions of the microfluidic device.

FIG. 14 shows a high-level diagram of hardware components of a system for transplantation of nucleic acids. The system includes a syringe pump 1411 for activating flow of fluid through tubing 1413 into and out of a microfluidic device 1415. Valves 1417 control the flow of fluid. Actuators 1419 directly or indirectly actuate the opening and closing of the valves 1417. A microcontroller 1421 controls the actuators. A microscope 1423 and camera 1425 capture visual data regarding phenomena occurring in the microfluidic device. Other sensors 1427 take sensor readings of these phenomena.

Figure 15:
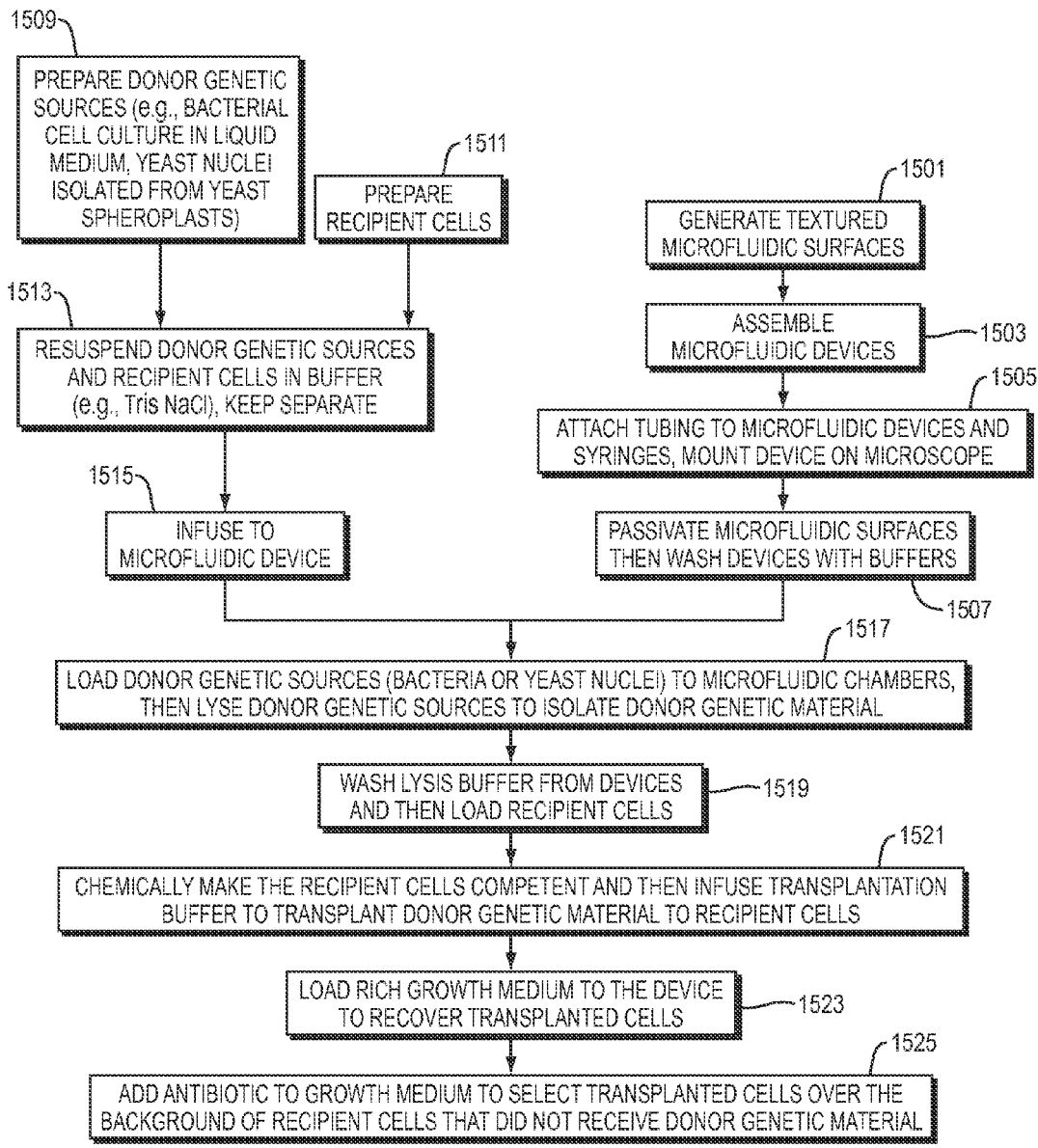
FIG. 15 shows a flow chart of steps in a process for transplantation of nucleic acids.

FIG. 15 shows a flow chart of steps in a process for transplantation of nucleic acids.

In the example shown in FIG. 15, preparation of the equipment includes: Generate textured microfluidic surfaces, such as by soft lithography (e.g. cast PDMS elastomeric devices from photoresist on silicon wafer) or by using an excimer laser to ablate glass cover slips 1501. Assemble microfluidic devices, such as by plasma bonding PDMS to glass, and by fusing glass surfaces together at 640° C. in muffle furnace 1503. Attach tubing to microfluidic device and syringe, and mount microfluidic device on microscope 1505. Passivate microfluidic surfaces and then wash microfluidic device with buffers 1507.

In the example shown in FIG. 15, preparation of the cells and donor genetic material includes: Prepare donor genetic sources (such as bacterial cell culture in liquid medium, or yeast nuclei isolated from yeast spheroplasts) 1509. Prepare recipient cells 1511. Resuspend donor cells in buffer and separately resuspend recipient cells in buffer (in both cases, for example, the buffer may include Tris NaCl) 1513. Infuse the donor cells into the microfluidic device, and separately infuse the recipient cells into the microfluidic device, keeping donor cells separate from the recipient cells 1515.

In the example shown in FIG. 15, events occurring in the microfluidic device include: Load donor cells (e.g., bacteria or yeast nuclei) to microfluidic chambers, then lyse donor cells to isolate donor genetic material 1517. Wash lysis buffer from the chambers, and then load recipient cells 1519. Infuse chemicals to make the recipient cells more competent and then infuse transplantation buffer to transplant donor genetic material into recipient cells 1521. Infuse nutrient-rich growth medium into the chambers, and allow the recipient cells to recover 1523. Add antibiotic to the growth medium to select transplanted cells over the background of recipient cells that did not receive donor genetic material 1525.

Figure 16:
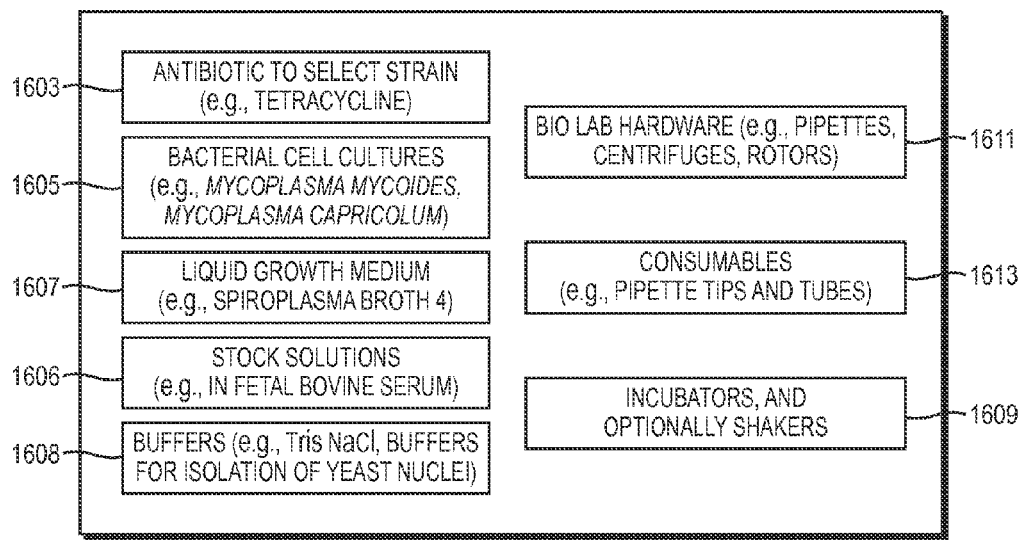
FIG. 16 is a diagram of materials and hardware used in transplantation of nucleic acids.

FIG. 16 is a diagram of materials and equipment used in transplantation of nucleic acids. Materials used to prepare bacterial cell cultures (e.g., *Mycoplasma mycoides, Mycoplasma capricolum*) include: antibiotic (e.g., tetracycline) to select strain 1603; bacterial cell cultures 1605; liquid growth medium (e.g., Spiroplasma broth 4, SP4) 1607; stock solutions (e.g., in fetal bovine serum) 1606; and buffers (e.g., Tris NaCl or buffers for isolation of yeast nuclei) 1608. Equipment used during cell preparation include 30° C. and 37° C. incubators, and shakers if needed 1609; bio lab hardware (e.g., pipettes, centrifuges, rotors) 1611; and consumables (e.g., tubes and pipette tips) 1613.

In some implementations, the donor genetic material comprises either (a) whole intact genomes, (b) plasmids, (c) or sequences shorter than plasmids.

In illustrative implementations, a buffer (e.g., a chemical competence buffer) is used to make cells more competent (ready for transplantation). In some cases, a chemical competence buffer destabilizes a membrane in a cell. Chemical competence buffers may include any combination of one or more of: (a) crowding agents such as polyethylene glycol (PEG), dextran, or Ficoll®; (b) divalent ions such as calcium chloride or magnesium chloride; (c) solvents such as dimethyl sulfoxide (DMSO) or ethanol; (d) nanoparticles, detergents, or surfactants; and (e) growth media such as LB medium, synthetic minimal media, and *mycoplasma* media such as Spiroplasma broth 4. In some cases, it is not necessary, prior to transplantation, to expose the donor cells to a chemical competence buffer. Once the donor cells are competent, a variety of different approaches may be used to trigger a transfer of nucleic acid into cells. In some cases, these approaches include one or more of: osmotic shock with a crowding agent (e.g., PEG, dextran, Ficoll®), temperature shock, electroporation, sonoporation, optoporation, lipofection, or co-precipitation.

In exemplary implementations, gentle and well-controlled physical and chemical manipulation of cells and long chains of nucleic acids occurs while the cells and long chains are confined in microfluidic channels or chambers, thereby keeping the long chains intact (lowering instances of breakage). In this way, microfluidic confinement increases yield of whole-genome transplantation as well as the yield and reproducibility of transformation using any length nucleic acid sequences including small plasmids.

In exemplary implementations, robust monitoring (e.g. long-term time resolved imaging with ability to track individual cells and genomes and their interactions) is achieved. Cell, nucleic acid and nucleic acid-cell interactions are controlled while the objects or events being monitored are confined in microfluidic channels or chambers. Control over the physicochemical conditions affecting nucleic-acid cell interactions (and determination of the optimal conditions to achieve rare phenomena such as whole genome transplantation) is achieved by microfluidic set up of gradients and imaging in real time.

In exemplary implementations, microfluidic architectures facilitate the in-depth, high throughput study and elucidation of the transplantation mechanism in action, thereby (i) allowing determination of the salient parameters for efficiency improvements and (ii) allowing transition to organisms relevant for medical or industrial biomanufacturing uses.

In exemplary embodiments, a versatile microfluidic platform allows for efficient transplantation of intact large genomes. This transplantation is achieved by the physical confinement of donor and recipient cells to microfluidic devices made of glass and polydimethylsiloxane (PDMS) comprising tubing connected to input and output openings that address trenches connected to chambers or channels of 1-100 micrometer dimensions. Combinations of main trenches (allowing high mass transfers) with smaller channels or chambers and interconnected 2D and 3D networks are such that they allow for the precise localization of cells, genomes and gradients of chemical factors. Computer controlled valves are used for the on-demand movement and modulation of each of the substances and physical conditions used in the transplantation process.

In one example cells are loaded into channels or chambers using gentle centrifugation and/or entropic crowding and/or physical compression forces (mediated by compressed gas or liquid flows delivered via flexible PDMS valves, through variable cross sectional areas geometries or other methods), as well as by diffusive and osmotic drivers such as selection of hyper/hypotonic solution gradients.

In an illustrative embodiment, a versatile microfluidic platform is configurable for: (a) loading of small numbers (from single cells to hundreds of cells) of donor cells (e.g. yeast or *mycoplasma* containing desired "donor genome" and containing one or more antibiotic resistance genes) into a large number of channels or chambers—achieved via centrifugation or diffusion; (b) setting up of a concentration gradient of lysing agent or simply perfusion of trench with buffer containing lysing agent at a single concentration to achieve lysis of trapped donor cells—avoiding shear forces associated with pipetting or agar plug allows genome to remain intact; (c) use of PEG or other selective crowding agent such that the genome of lysed cells remains trapped in channels or chambers while the cytoplasm and organelles are washed away by streaming solution; (d) loading of recipient cells into channels or chambers containing the naked genome previously isolated, including the case where these have been treated with cross-linking agents making recipient native genome incapable of dividing; (e) setting up a one dimensional or two dimensional concentration gradient for a "fusion/transplantation" buffer or simply perfusing all channels/chambers with a buffer of constant concentration aimed at promoting the insertion of the isolated donor genomes into the recipient cells; and (f) automated or manual extraction of the transplantation product cells to create new colonies including scaled-up colonies appropriate for pharmaceutical and other biomanufacturing applications.

This invention has many practical applications. Here are some non-limiting examples:

In exemplary implementations: (i) microfluidic platforms for manipulating and observing individual cells and genomes are used to control the physical and chemical environment of individual, microscale prokaryotic and eukaryotic cells; and (ii) smaller nanofluidic devices are used to study single, nanoscale DNA molecules. These miniaturized fluidic formats are used (a) to probe these systems in real-time using sensitive and quantitative light microscopy techniques, (b) to eliminate shearing forces that can easily damage large DNA molecules in bulk solution, (c) to keep a genome intact and packed while lysing the cell and/or nuclear membrane and allowing the cytoplasm and organelles to be washed away, (d) to mediate the cell-genome interaction via confinement, (e) to control the chemical environment through well-known fluidic techniques, and (f) to achieve parallelization for high-throughput transplantation and multiplexed screening of experimental conditions, all of which facilitate high yield, generalized transplantations.

In exemplary implementations, the interaction between donor genomes and recipient cells is precisely controlled for successful genome transplantation for a variety of bacterial species. More broadly, in some implementations, the microfluidics technology and methods described here is used for genome transplantation for prokaryotic or eukaryotic single cells. For example, in illustrative implementations, this invention can: (a) microfluidically isolate YCPs from yeast nuclei prior to subsequent transplantation on-chip; and (b) isolate human artificial chromosomes constructed in yeast and install these chromosomes into suitable recipient cells.

In exemplary implementations of this invention, microfluidic screening of growth conditions is used to determine the optimal growth conditions for bacteria and other cells that are difficult to culture in the lab. This is applicable to the so called "unculturable" microbes, as well as extremophiles, *algae* and others.

In exemplary implementations, this invention can transplant complete or near complete genomes for unknown bacteria (e.g., genomes which have been synthesized by microbiome shotgun sequencing) into appropriate recipient cells to generate those organisms.

In some implementations, recoded genomes are isolated and installed in a suitable recipient cell or cellular milieu, thereby creating industrially useful organisms that are resistant to all bacteriophages and at the same time safe.

In some implementations, the donor genetic material includes extended and alternative base sets, or, when expressed, creates non-canonical amino acids.

In some implementations, a functionalization/hybridization/folding step is performed in a microfluidic device. In other implementations, this step is performed outside the microfluidic device, and then the microfluidic device is used (a) to screen or optimize materials and conditions, or (b) to read out high throughput or multiplexed signals (e.g., from reporting dyes, labels, or antibodies).

In some implementations, a microfluidic device performs one or more of the following tasks: handling, extraction, insertion, transplantation, manipulation, editing, splicing, ligating, functionalizing, or decorating with dyes and labels. In some cases, the dyes or labels comprise one or more of the following: ion channel and chemical, biological. nanostructured and fluorescent dyes and labels including nanodiamonds, FRET sets as well as dyes, tags, receptors (including cytosolic and cellular and nuclear membrane receptors, pores or channels, including membrane receptors, pores or channels modified separately or by the microfluidic device for secondary and tertiary conformation, aggregation, polymerization or solubility).

Processors

In exemplary implementations of this invention, one or more electronic processors are specially adapted: (1) to control the operation of, or interface with, hardware components of a system comprising a microfluidic device and related sensors, including to control or interface with any pumps, valves, actuators, microscope, imaging sensor, other sensor, or any actuator for moving a valve or a microscope; (2) to analyze data gathered by a microscope or other sensors; (3) to receive signals indicative of human input, (4) to output signals for controlling transducers for outputting information in human perceivable format, and (5) to process data, to perform computations, to execute any algorithm or software, and to control the read or write of data to and from memory devices. The one or more processors may be located in any position or positions within or outside of the system. For example: (a) at least some of the one or more processors may be embedded within or housed together with other components of the system, such as with actuators or sensors, and (b) at least some of the one or more processors may be remote from other components of the system. The one or more processors may be connected to each other or to other components in the system either: (a) wirelessly, (b) by wired connection, or (c) by a combination of wired and wireless connections. For example, one or more electronic processors (e.g., 1431, 1433, 1435) may be housed in a computer 1429 or microcontroller 1421.

Definitions

The terms "a" and "an", when modifying a noun, do not imply that only one of the noun exists.

A "big nucleic acid" means a nucleic acid molecule that includes at least 20,000 nucleotides per strand of the molecule. For example, a "big nucleic acid" molecule may (so long as the molecule includes at least 20,000 nucleotides per strand) comprise all or part of a chromosome. A "big nucleic acid" that is double-stranded includes at least 20,000 base pairs.

The term "camera" shall be construed broadly. Here are some non-limiting examples of a "camera": (a) an optical instrument that records images; (b) a digital camera; (c) a video camera; (d) a camera that uses photographic film or a photographic plate; (e) a light field camera; (f) an imaging system, (g) a light sensor; (h) apparatus that includes a light sensor or an array of light sensors; or (i) apparatus for gathering data about light incident on the apparatus.

A "cell portal" means an orifice that has a dimension (e.g., diameter or width), from an inner rim of the orifice to another inner rim of the orifice, of at least 180 nm.

The term "channel" shall be broadly construed. For example, in some cases, a channel is enclosed so that it is not exposed to ambient atmosphere.

The term "comprise" (and grammatical variations thereof) shall be construed broadly, as if followed by "without limitation". If A comprises B, then A includes B and may include other things.

The term "contain" (and grammatical variations thereof) shall be construed broadly, as if followed by "without limitation". If A contains B, then A contains B and may contain other things. To say that a fluid "contains" an object means that the object is partially or wholly immersed, suspended, dissolved or otherwise located in the fluid, and does not imply that the fluid confines or restrains movement of the object.

"Dead-end loading" means movement of fluid through an orifice into a volume, while fluid exits the volume by diffusion through a layer or wall.

"Defined Term" means a term that is set forth in quotation marks in this Definitions section.

"Diffusion" is not limited to particles of a particular size. For example, molecules of a solute may diffuse from a region with a higher concentration of the molecules to a region with a lower concentration of the molecules. Or, for example, biological cells may diffuse from a region with a higher concentration of the cells to a region with a lower concentration of the cells. Effusion, permeation and osmosis are non-limiting examples of "diffusion", as that term is used herein.

"Donor source" means a physical object from which a nucleic acid is obtained, by removing, releasing, or extracting the nucleic acid from the physical object. For example, in some cases, the physical object is (i) a biological cell, (ii) a yeast nucleus, or (iii) an encapsulated nucleic acid. For example, in some cases, a nucleic acid from a "donor source" is transplanted into a recipient cell.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

The term "fluid" shall be construed broadly, and includes gases and liquids.

The term "for instance" means for example.

"Herein" means in this document, including text, specification, claims, abstract, and drawings.

The terms "horizontal" and "vertical" shall be construed broadly. For example, "horizontal" and "vertical" may refer to two arbitrarily chosen coordinate axes in a Euclidian two dimensional space, regardless of whether the "vertical" axis is aligned with the orientation of the local gravitational field. For example, a "vertical" axis may oriented along a local surface normal of a physical object, regardless of the orientation of the local gravitational field.

Unless the context clearly indicates otherwise: (1) the term "implementation" means an implementation of this invention; (2) the term "embodiment" means an embodiment of this invention; and (3) the phrase "in some cases" means in some implementations of this invention.

The term "include" (and grammatical variations thereof) shall be construed broadly, as if followed by "without limitation"

An "isolated nucleic acid" means a nucleic acid that is surrounded by neither an outer cell membrane nor a nuclear membrane.

A "large nucleic acid" means a nucleic acid molecule that includes at least 100,000 nucleotides per strand of the molecule. For example, a "large nucleic acid" molecule may (so long as the molecule includes at least 100,000 nucleotides per strand) comprise all or part of: a genome, a circular bacterial chromosome, a circular archeal chromosome, or a eukaryotic chromosome. A "large nucleic acid" that is double-stranded includes at least 100,000 base pairs.

"Large nucleic acid transplantation" means transplantation of a large nucleic acid into a biological cell.

A "lysis agent" means a physical stimulus that triggers lysis of a biological cell. In some cases, a "lysis agent" is a substance.

The term "magnitude" means absolute value.

A "microfluidic chamber" means a chamber that has an inner volume that is less than or equal to one microliter. For purposes of the immediately preceding sentence, when computing the inner volume, the chamber shall be treated as if its inner wall(s) were not pierced by any orifice.

The term "nucleic acid" shall be construed broadly. Here are some non-limiting examples of a "nucleic acid": deoxyribonucleic acid (DNA), ribonucleic acid (RNA), peptide nucleic acid, morpholino- or locked nucleic acid, glycol nucleic acid, threose nucleic acid, or a portion or fragment of a nucleic acid, which portion or fragment includes at least four nucleotides. The term "nucleic acid" is not limited to naturally occurring nucleic acids. All or part of a "nucleic acid" may be unnatural. For example, a nucleic acid may include one or more unnatural nucleobases, one or more unnatural nucleotides, or one or more unnatural base pairs.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or can be ignored.

As used herein, the term "set" does not include a so-called empty set (i.e., a set with no elements). Mentioning a first set and a second set does not, in and of itself, create any implication regarding whether or not the first and second sets overlap (that is, intersect).

As used herein, a "subset" of a set consists of less than all of the elements of the set.

"Such as" means for example.

Transplantation" means a process in which a nucleic acid molecule that is external to a biological cell enters the cell. Here are some non-limiting examples of "transplantation": transformation, transfection, transduction, and conjugation. "Transplantation" is not limited to an entire genome or to any particular size or type of nucleic acid. For example, a nucleic acid molecule that undergoes "transplantation" may be of any type or size and may include any number of base pairs or nucleotides. Also, for example, a nucleic acid molecule that undergoes transplantation may comprise all or part of a chromosome. "Transplantation" is not limited to any particular type of biological cell. "Transplantation" is not limited to any particular technique for introducing an external nucleic acid molecule into a biological cell. For example, in some cases, "transplantation" is triggered by one or more of the following: a crowding agent, heat shock, electroporation, optoporation, lipofection, or calcium phosphate or calcium chloride co-precipitation.

A "transplantation agent" means a physical stimulus that triggers transplantation. In some cases, a "transplantation agent" is a substance.

A "transplanted cell" means (1) a recipient cell that has undergone transplantation, during which one or more nucleic acids entered the cell, or (2) a cell that is a descendant (e.g., clone) of such a recipient cell.

The term "trigger" shall be construed broadly. Here are some non-limiting examples of A triggering B. A "triggers" B if, for example: (a) A causes B; (b) A increases the temporal rate at which B occurs; or (c) A increases the percentage of times that B is an outcome of a process or event.

"Unnatural" means not occurring in nature. For example, a synthesized compound is unnatural if it does not occur in nature.

Spatially relative terms such as "under", "below", "above", "over", "upper", "lower", and the like, are used for ease of description to explain the positioning of one element relative to another. The terms are intended to encompass different orientations of an object in addition to different orientations than those depicted in the figures.

Except to the extent that the context clearly requires otherwise, if steps in a method are described herein, then: (1) steps in the method may occur in any order or sequence, even if the order or sequence is different than that described; (2) any step or steps in the method may occur more than once; (3) different steps, out of the steps in the method, may occur a different number of times during the method, (4) any step or steps in the method may be done in parallel or serially; (5) any step or steps in the method may be performed iteratively; (5) a given step in the method may be applied to the same thing each time that the particular step occurs or may be applied to different things each time that the given step occurs; and (6) the steps described are not an exhaustive listing of all of the steps in the method, and the method may include other steps.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, or possessive forms, or different declensions, or different tenses. For example, the definition of the noun "diffusion" also applies to the verb "diffuse", after taking into account the difference in grammatical form. For example, the definition of the noun "transplantation" also applies to the verb "transplant", after taking into account the difference in grammatical form. In each case described in this paragraph, Applicant is acting as Applicant's own lexicographer.

Variations:

In one aspect, this invention is a method comprising, in combination: (a) moving one or more lysis agents into a microfluidic chamber to trigger lysis or one or more donor sources, which lysis occurs inside the chamber; (b) moving the lysis agents out of the chamber; (c) moving one or more recipient cells into the chamber; and (d) moving one or more transplantation agents into the chamber to trigger transplantation of nucleic acids into the recipient cells, which nucleic acids were, prior to the lysis, in the donor sources, and which transplantation occurs inside the chamber; wherein, at all times during the method, the chamber has one or fewer cell portals. In some cases, the moving in steps (a), (b), (c) and (d) of the method is by dead-end loading of the chamber or by diffusion. In some cases, neither the recipient cells nor the nucleic acids are attached to a wall of the chamber prior to or during the transplantation. In some cases, the nucleic acids are large nucleic acids. In some cases, the chamber forms a cavity that has a volume of less than one nanoliter. In some cases: (a) the cell portal has first dimension, which first dimension is the maximum inner rim-to-inner rim distance of the cell portal; (b) the chamber is elongated and has a longitudinal axis along the length of the chamber; (c) the chamber has a second dimension, which second dimension is the maximum inner wall-to-inner wall distance of the chamber in any direction that is perpendicular to the longitudinal axis; and (d) the first dimension is less than the product of 0.8 times the second dimension. Each of the cases described above in this paragraph is a non-limiting example of the method described in the first sentence of this paragraph, and is also a non-limiting example of an embodiment of this invention that may be combined with other embodiments of this invention.

In another aspect, this invention is a process which comprises moving transplantation agents into a microfluidic chamber to trigger transplantation of nucleic acids into recipient cells, wherein: (a) the transplantation occurs in the chamber; and (b) no net fluid flow into or out of the chamber occurs during the diffusing and transplantation, except (i) net fluid flow, if any, that enters the chamber by diffusion and exits the chamber in any way, or (ii) net fluid flow, if any, that exits the chamber by diffusion and enters the chamber in any way. In some cases: (a) the process further comprises mixing a first fluid and a second fluid; (b) immediately prior to the mixing, (i) the first fluid contains the recipient cells but not the nucleic acids, and (ii) the second fluid contains the nucleic acids but not the recipient cells; and (c) no net fluid flow into or out of the chamber occurs during the mixing, except (i) net fluid flow, if any, that enters the chamber by diffusion and exits the chamber in any way, or (ii) net fluid flow, if any, that exits the chamber by diffusion and enters the chamber in any way. In some cases, lysis agents are used to trigger lysis of donor sources, before the mixing. In some cases, the nucleic acids are big nucleic acids. In some cases, at all times during the process, fluid flow, if any, through each respective cell portal, if any, of the chamber has a Reynolds number that is less than ten. In some cases, the moving of transplantation agents is by dead-end loading or by diffusion. In some cases, at all times during the process, net fluid flow, if any, through each respective cell portal, if any, of the chamber is at a velocity of less than 10 microns per minute. Each of the cases described above in this paragraph is an example of the process described in the first sentence of this paragraph, and is also an example of an embodiment of this invention that may be combined with other embodiments of this invention.

In another aspect, this invention is an apparatus comprising, in combination: (a) a first channel; (b) a set of microfluidic chambers, such that each respective chamber in the set of chambers has only one cell portal and is connected, via the cell portal, to the first channel; and (c) one or more valves for controlling fluidic movement in the first channel, such that transplantation agents in the first channel move into the first set of chambers to trigger transplantation of nucleic acids into cells, which transplantation occurs in the first set of chambers. In some cases: (a) the apparatus includes a second channel and a third channel; and (b) one end of the first channel is connected to the second channel and another end of the first channel is connected to the third channel, such that flowing a solution at a first concentration of a solute in the second channel and a second, different concentration of the solute in the third channel creates a concentration gradient of the solute along the first channel. In some cases: (a) the apparatus does not include any flow channel which is in the shape of a loop and which comprises a cavity formed by one or more chambers in the set; or (b) at all times during the transplantation, net fluid flow around such a flow channel does not occur. In some cases, the nucleic acids are large nucleic acids. In some cases, (a) a specific chamber in the set of chambers is elongated along a first longitudinal axis; (b) the first channel is elongated along a second longitudinal axis, and (c) the first longitudinal axis is at an angle of at least 45 degrees relative to the second longitudinal axis. In some cases, the apparatus includes: (a) an additional channel, which additional channel is adjacent to one or more chambers in the set of chambers; and (b) a pump for changing pressure in the additional channel, such that pressure in the additional channel is less than pressure in the one or more chambers. In some cases, at least one sphere exists, such that (i) the cell portal subtends less than 3.14 steradians as seen from the center of the sphere, and (ii) the center of the sphere is located in the interior of the chamber. Each of the cases described above in this paragraph is an example of the apparatus described in the first sentence of this paragraph, and is also an example of an embodiment of this invention that may be combined with other embodiments of this invention.

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also within the scope of the present invention. Numerous modifications may be made by one of ordinary skill in the art without departing from the scope of the invention.

What is claimed is:

1. A method comprising, in combination:
   (a) providing a microfluidic chamber;
   (b) moving, into the chamber, one or more donor sources that contain nucleic acids;
   (c) moving one or more lysis agents from a region external to the chamber into the chamber;
   (d) triggering, by the lysis agents, lysis of the one or more donor sources, such that the lysis occurs inside the chamber;
   (e) moving the lysis agents out of the chamber;
   (f) moving one or more recipient cells into the chamber;
   (g) moving one or more transplantation agents into the chamber; and
   (h) triggering, by the transplantation agents, transplantation of the nucleic acids into the recipient cells, such that the transplantation occurs inside the chamber;
   wherein at all times during steps (a), (b), (c), (d), (e), (f), (g) and (h), no more than one cell portal of the chamber exists.

2. The method of claim 1, wherein the nucleic acids are large nucleic acids.

3. The method of claim 1, wherein a cavity is located in the chamber, which cavity has a volume of less than one nanoliter.

4. The method of claim 1, wherein the moving in steps (c), (e), (f) and (g) is by dead-end loading of the chamber or by diffusion.

5. The method of claim 1, wherein neither the recipient cells nor the nucleic acids are attached to a wall of the chamber prior to or during the transplantation.

6. The method of claim 1, wherein:
   (i) the cell portal has first dimension, which first dimension is the maximum inner rim-to-inner rim distance of the cell portal;
   (ii) the chamber is elongated and has a longitudinal axis along the length of the chamber;
   (iii) the chamber has a second dimension, which second dimension is the maximum inner wall-to-inner wall distance of the chamber in any direction that is perpendicular to the longitudinal axis; and
   (iv) the first dimension is less than the product of 0.8 and the second dimension.

7. The method of claim 1, wherein:
   (i) the chamber is elongated along a first longitudinal axis;
   (ii) the cell portal is an opening into a first channel that is external to the chamber;
   (iii) the first channel is elongated along a second longitudinal axis; and
   (iv) the first longitudinal axis is at an angle of at least 45 degrees relative to the second longitudinal axis.

8. The method of claim 1, wherein at least one sphere exists, such that (i) the cell portal subtends less than 3.14 steradians as seen from the center of the sphere, and (ii) the center of the sphere is located in the interior of the chamber.

* * * * *